(12) United States Patent
Gordon et al.

(10) Patent No.: US 6,852,289 B2
(45) Date of Patent: Feb. 8, 2005

(54) METHODS AND APPARATUS FOR DETERMINING ANALYTES IN VARIOUS MATRICES

(75) Inventors: Virginia C. Gordon, Huntington Beach, CA (US); Bennett W. Root, Jr., Huntington Beach, CA (US); Barbara J. Peasley, Brea, CA (US); John F. Elias, Buena Park, CA (US); John T. Sorensen, Costa Mesa, CA (US); Michael Mittelstein, Laguna Niguel, CA (US); Soheila Mirhashemi, Laguna Niguel, CA (US)

(73) Assignee: Saftest, Inc., Tempe, AZ (US)

( * ) Notice: Subject to any disclaimer, the term of this patent is extended or adjusted under 35 U.S.C. 154(b) by 94 days.

(21) Appl. No.: 09/817,446

(22) Filed: Mar. 26, 2001

(65) Prior Publication Data

US 2003/0064423 A1 Apr. 3, 2003

Related U.S. Application Data

(63) Continuation of application No. 09/183,157, filed on Oct. 30, 1998, now abandoned, which is a continuation of application No. 09/058,238, filed on Apr. 9, 1998, now abandoned, which is a continuation-in-part of application No. 08/723,636, filed on Oct. 2, 1996, now Pat. No. 5,958,714.
(60) Provisional application No. 60/063,038, filed on Oct. 22, 1997.

(51) Int. Cl.$^7$ .................... B01L 11/00; B01D 24/00; C12M 3/00
(52) U.S. Cl. ............. 422/101; 435/287.1; 435/288.4; 435/288.5; 210/335
(58) Field of Search .................. 436/518; 435/7.92, 435/287.1, 288.4, 288.5, 7.1; 422/100, 101, 104, 70; 210/335

(56) References Cited

U.S. PATENT DOCUMENTS

| 4,407,973 A | * | 10/1983 | Cole et al. ................. 435/7 |
| 4,493,815 A | * | 1/1985 | Fernwood et al. ......... 422/101 |
| 4,797,259 A | * | 1/1989 | Matkovich et al. ........ 422/101 |
| 4,902,481 A | * | 2/1990 | Clark et al. ............... 422/101 |

(List continued on next page.)

*Primary Examiner*—Padmashri Ponnaluri
*Assistant Examiner*—My-Chau Tran
(74) *Attorney, Agent, or Firm*—Robert D. Buyan; Stout, Uxa, Buyan & Mullins, LLP

(57) ABSTRACT

Methods and apparatus for qualitatively or quantitatively determining one or more analytes in matrices such as foods, biological fluids, etc. An embodiment for determination of a single analyte comprises a sample receiving vessel, a first membrane and a reagent-containing well. The prepared sample passes through the first membrane whereby extraneous matter is removed, and a filtrate enters the reagent-containing well to provide a filtrate-reagent admixture from which the analyte may be determined. An embodiment for determination for multiple analytes includes one or more additional membranes in series with the first membrane, each such additional membrane being operative to capture one or more analytes. Each of the additional analytes may then be eluted from the membrane upon which it has been captured, into a separate reagent-containing well to provide eluant-reagent admixture from which each desired analyte may be determined. Formulations for preparation additives are also included. Additionally, there's provided an embodiment of above-described invention for determination of an analyte which is present in a matrix at low (e.g., sub-detectable) levels, wherein the filter of the apparatus is utilized to capture and concentrate the analyte, to provide a filtrate-reagent admixture wherein the analyte is present at detectable concentration.

7 Claims, 28 Drawing Sheets

U.S. PATENT DOCUMENTS

| | | | | |
|---|---|---|---|---|
| 4,948,564 A | * | 8/1990 | Root et al. | 422/101 |
| 5,039,493 A | * | 8/1991 | Oprandy | 210/224 |
| 5,283,039 A | * | 2/1994 | Aysta | 422/104 |
| 5,342,581 A | * | 8/1994 | Sanadi | 422/101 |
| 5,401,637 A | * | 3/1995 | Pocock | 435/7.1 |
| 5,418,171 A | * | 5/1995 | Kimura et al. | 436/518 |
| 5,578,459 A | * | 11/1996 | Gordon et al. | 135/29 |
| 5,603,899 A | * | 2/1997 | Franciskovich et al. | 422/100 |
| 5,807,523 A | * | 9/1998 | Watts et al. | 422/64 |
| 5,958,714 A | * | 9/1999 | Gordon et al. | 435/7.92 |

* cited by examiner

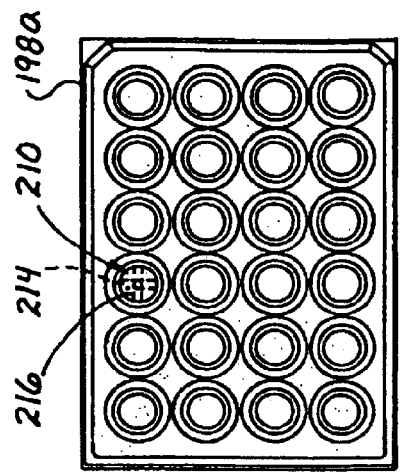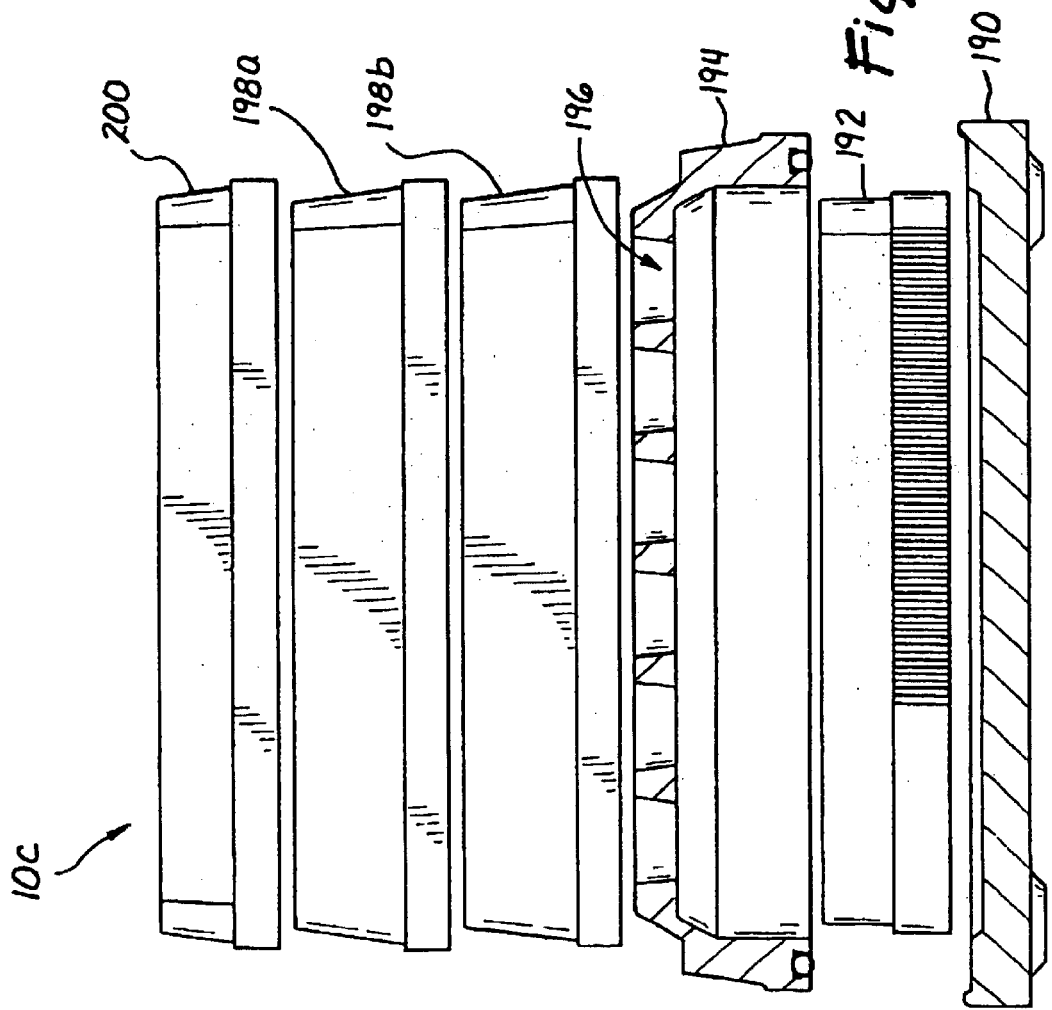

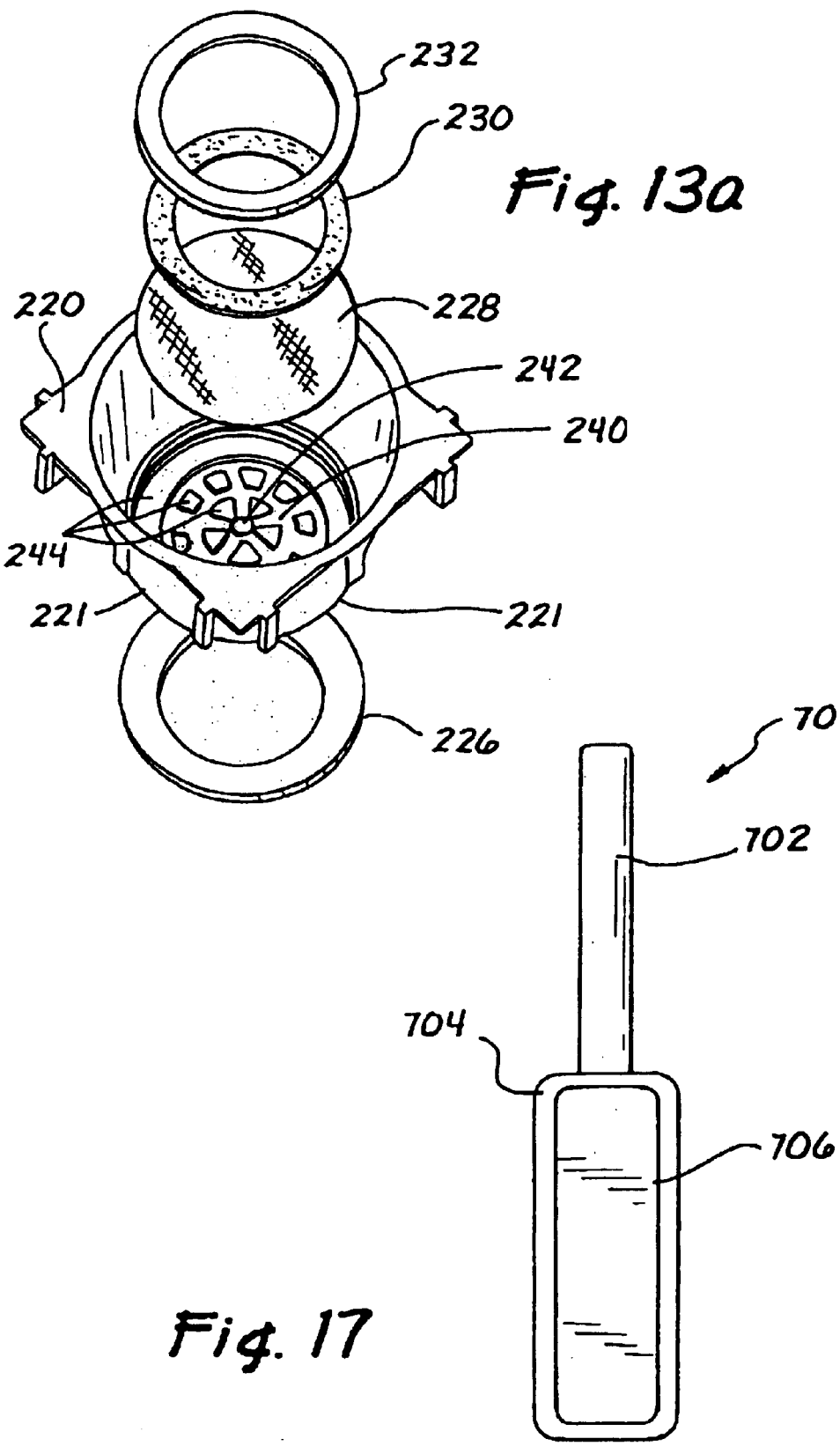

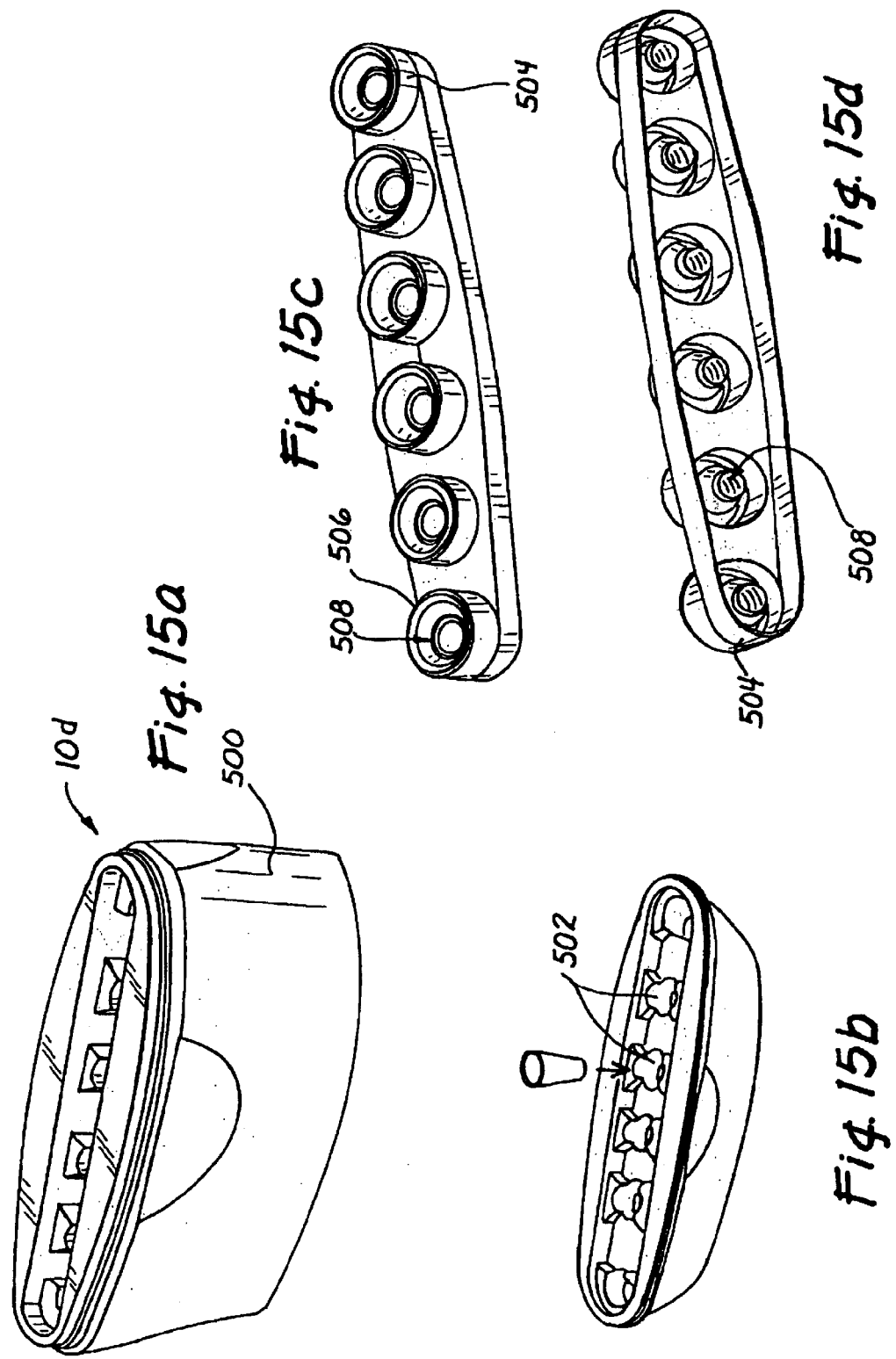

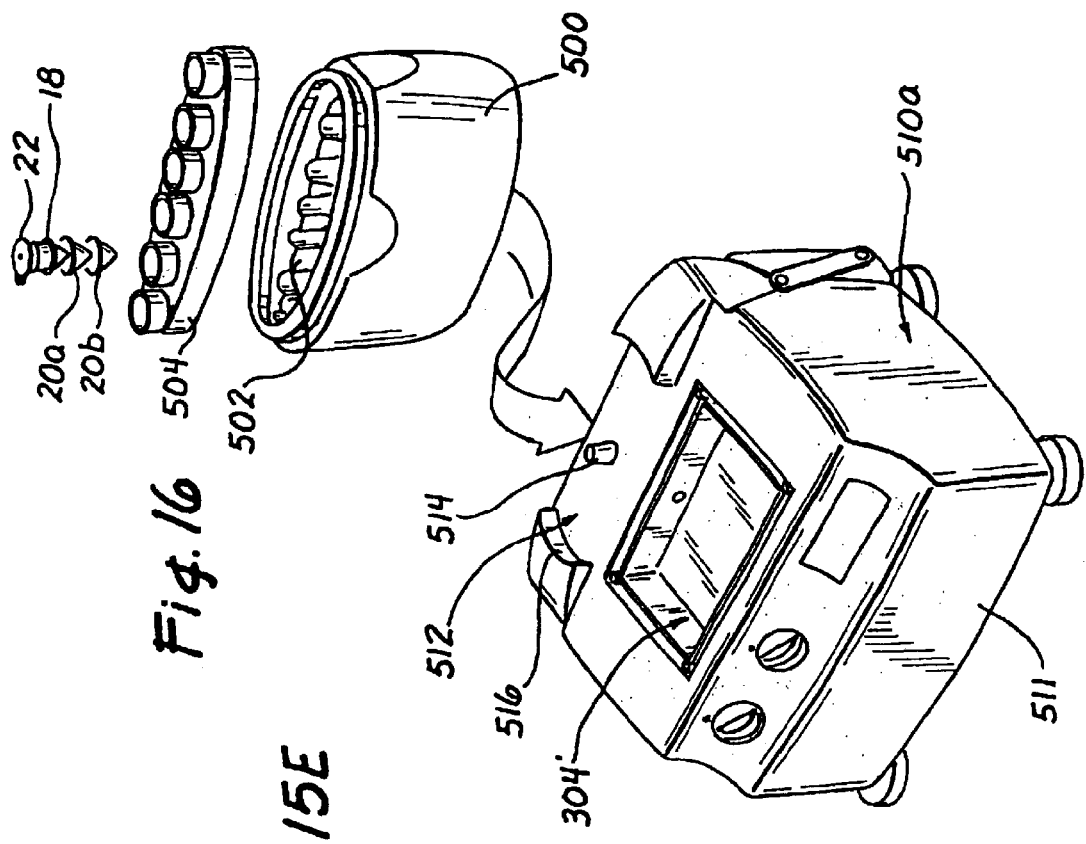
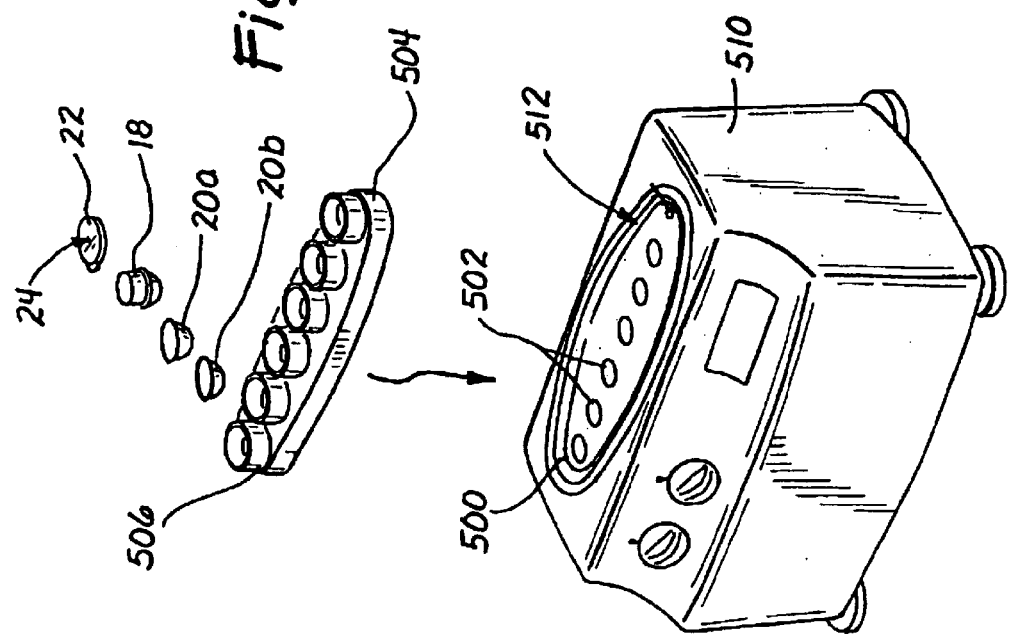

TABLE I

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 1. | FFA*, FFA^ | Oil<br>Fish<br>Bakery<br>Fast Food<br>Oil in Frying | With or without any other analytes or membrane | | | | XO | | | | Spectral 570 or (visual) or color wheel | |
| | | | MCE .45 or Durapore .45 to remove particulates | | | | | | | | | |
| 2. | LPO/FFA | Oil or olive | MCE | Nylon linked decasyl polymers or silica to bind LPO | | | XO | XO and Fe+ (acidified) | | | Spectral | |
| 3. | LPO/FFA* | Oil | MCE | Silica | | | XO | reduced haemoglobin | | | Spectral | |
| 4. | LPO/FFA/MDA | Oil/Seafood | MCE | Silica | Diethylamine | | XO | XO (Fe+ Acidified) | MI | | Spectral | |
| 5. | LPO, MDA, FFA after oxidative stress | Oil | MCE | Silica | Diethylamine | | XO | XO (Fe+ Acidified) | MI | | % change proportional to shelf life Use visible meas. Color change | |
| 6. | LPO, MDA, FFA After oxidative stress | Oil<br>Fish<br>Bakery | MCE to remove particulates | Silica to bind LPO | Diethylamine to bind<br>MDA | | XO | XO (Fe+ acidified) | MI | | Spectral | |
| 7. | LPO after oxidative stress | Fish<br>Oil | MCE | MCE | | | XO (Fe+ acidified) | | | | Spectral | |

1. New Tests

Fig. 18A

1. New Tests

| | Analytes | Typical Matrix | Membranes | | | | | Reagents | | | | Detection Method | Comments |
|---|---|---|---|---|---|---|---|---|---|---|---|---|---|
| | | | $M_1$ | $M_2$ | $M_3$ | $M_4$ | | $R_1$ | $R_2$ | $R_3$ | $R_4$ | | |
| 8. | FFA after Oxidative Stress | Oil | MCE | | | | | XO | | | | Spectral | |
| 9. | Polyphenol/LPO | Oil, Olives, Fruit, vegetables | MCE | Silica to bind LPO | | | | Folin (Ciocalteau) | XO (Fe$^+$ acidified) | | | Spectral | |
| 10. | Polyphenol | Oil | MCE | | | | | Folin (Ciocalteau) | | | | Spectral | |
| 11. | Polyphenol and FFA | Oil Fruit Vegetables | MCE | Carboxymethyl to bind Polyphenol | | | | XO | Folin Ciocalteau | | | Spectral | |
| 12. | Polyphenol MDA/LPO/FFA | Oil | 0.8 um to bind particulates | Silica or nylon with lipid solubilizing decisyler to bind LPO | Caroxy methyl weakly acidic membrane to bind polyphenols | diethylamine to bind MDA | | XO | XO (Fe$^+$ acidified) | Folin (iocalteau) | MI | Spectral | |
| 13. | LPO Ratio for Antioxidant Status | Oil Fruit Vegetable | MCE | | | | | XO/Fe+ acidified | | | | Spectral | |
| 14. | Unsaturated linkage/LPO Value | Oil | MCE | Lipid solubilizing polymer attached nylon bind LPO | | | | $I_3 \rightarrow I_2$ | XO (acidified Fe) | | | Spectral | |
| 15. | Unsaturated linkage, MDA | Oil | MCE | diethylamine | | | | $I_3 \rightarrow I_2$ | MI | | | Spectral | |
| 16. | LPO, FFA, Histamine | fish beverage | MCE | Sulfonic Acid | Silica | | | XO | DAO and XO/Fe$^+$ acidified | XO/Fe$^+$ acidified | | Spectral | |

Fig. 18B

1. New Tests

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 17. | LPO/FFA/MDA | Fish beverage | MCE for particulates | Diethylamine to bind aldehydes for MDA | Lipid solubilizing polymer bound nylon to bind LPO | | XO test for FFA | MI test for MDA | XO (Fe$^+$ acidified) LPO | | Spectral | |
| 18. | LPO/Histamine** | fish cheese sausage | MCE | Biodyne C or Sartobind Q for histamine binding | | | XO Fe$^+$ acidified | diamine oxidase and XO Fe (acidified) | | | Spectral | |
| 19 A | Polymer vs. non-polymer triglycerides | Cooking Oils | Membrane with MW Cutoff 500 | | | | Lipase with glycerol kinase + | detect H$_2$O$_2$ with chromogen | | | Spectral | |
| 19 B | Polymer vs. non-polymer Oxidized trigly | Cooking Oil | MW cutoff 500 | | | | Lipase/glycerol 3 PO$_4$ oxidase | | | | Spectral | |
| 20. | Mycotoxins1 Mycotoxins2 Mycotoxins3 | Grain | MCE | mab bound NH$_2$ on regen cellulose | mab bound NH$_2$ on regen cellulose | mab bound NH$_2$ on regen cellulose | Mycotoxin1 enzyme conjugate | Mycotoxin2 enzyme conjugate | Mycotoxin3 enzyme conjugate (peroxidase mycotoxin conjugate) Measure H$_2$O$_2$ produced | | Spectral | |
| 21. | MDA/Sulfite | beer wine | MCE Prefilter or versapor prefilter | IDA to remove pigments and metals | Sartobind Q to bind aldehydes | | Fe$^{+3}$ (XO) → Fe$^{+2}$ (XO) blue → yellow For sulfite | MI for MDA | | | Spectral | |
| 22. | ATP Separation from ADP & AMP | fish other living material degradation | MCE Prefilter or negative adsorber | Diethylamine | | | ATP detected by bioluminescence detection luminol | ADP + AMP by bioluminescence detection luminol | | | Spectral | |

Fig. 18C

I. New Tests

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 23. | Histidine/Hist amine | fish | MCE | Carboxymethyl to bind histamine | | | TBPB detect histidine Tetrabromph enol blue | DAO + HRP + Methylene blue Detect Histamine | | | Spectral | |
| 24. | Histamine | wine, fish | Iminodi aceetic acid to (bind pigments) remove metals | IDA membrane to bind metal | | | DAO + XO Fe+ acidified | | | | Spectral | |
| 25. | Separation histamine* from all rest amines | Fish Sausage Cheese | Iminodi acetic acid remove metals | Sulfonic acid membrane bind other amines | | | DAO + XO Fe+ acidified | measure rest amines using Xylidyl blue | | | Spectral | |
| 26. | Total Polar Compounds | Cooking Oil | Silica to bind polar | | | | quantitate non-polar lipase and *** | quantitate polar lipase *** | | | Spectral | |
| 27. | Total Polar Compounds | Cooking Oil | Bind non-polar to hydrophobic membrane | | | | quantitate polar *** | quantitate non-polar *** | | | Spectral | |
| 28. | FFA or biliary acids | plasma or serum cows, huma ns | MCE to remove rbc etc. lipo proteins | | | | XO to test for FFA | | | | Spectral | |

* Proprietary

** After Stress

*** lipase → glycerol and ATP → glycero kinase and pyruvate kinase lactate dehydrogenase ^called acidity value fish, bakery, wine

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 29. | Polyphenol/F FA for prediction of adulteration | Oils | MCE | Carboxymethyl | | | XO | Folin Ciocalteau | | | Spectral | |
| 30. | Polyphenol/F FA LPO to predict adulteration & aging | Oils | MCE | Carboxymethyl to bind polyphenol | Silica | | XO | XO (Fe⁺ acidified) | Folin Ciocalteau | | Spectral | |
| 31. | Polyphenol/F FA to predict adulteration | Oils | MCE | Carboxymethyl | | | XO | Folin Ciocalteau | | | Spectral | |
| 32. | LPO/M DA/Acidity Irradiation | Oils Fish | MCE | Silica | diethylamine | | XO | XO Fe⁺ (acidified) | MI | | Spectral | |
| 33. | To Predict time for mycotoxin growth | grain | MCE | | | | XO (Fe⁺ acidified) | | | | Spectral | |
| 34. | FFA distribution | Oil predigested with lipase | MCE | Mab₂ to Oleic | Mab₂ Stearic | Mab₃ - Linoleic | XO | XO | XO | | Spectral | Same ratio predict oil type oleic/mexic2/li noleic3 |
| 36. | Polyphenol/F FA/TG | Oil | MCE | Strong acid sulfonic bind ROH⁺ | Lipid solubilizing polymer bound nylon to lipid peroxides | | XO | Folin Ciocalteau for polyphenol | Enzymatic determination triglyceride = Tg with lipase as in 19A | | Spectral | |
| 37. | Anions | Beer | MCE | IDA | | | flush Fe Cl, replace anions change color | | | | Spectral | |
| 38. | Aldehyde, bisulfites | Beer | MCE | diethylamine | | | Fe⁺³ (XO) reduced by bisulfite | MI | | | Spectral | |
| 39. | Protein, aldehyde | Beer | MCE | diethylamine | | | Coomassie Blue for protein | MI | | | Spectral | |

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 50. | Tetracycline Antibiotics in milk | Milk | MCE | decasilyl coated membrane | | | direct read at 365 nm | | | | 365nm Spectral | |
| 51. | Aflatoxin | Milk and Aflatoxin Conjugate | MCE | | | | Enzyme substrate = peroxidase aflatoxin conjugate and urea peroxide and tetramethybenzidine chromogen | | | | Spectral | |

Fig. 18F

PRO = Polyphenol

Others

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 52. | Microbes | Food | Versapor Particulates | IGN-6 binds microbes | | | Direct | | | | Reflectance | |
| 53. | Metals | Food | Versapor Particulates | IDA to bind Metal | | | Test for metals Zircon Zincon + Metal → deep blue | | | | Spectral | |

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 54. | Any Analytes | Food | Stacked bundle .8, .45 of M1 + M2++ | | | | Any of above | | | | Spectral | |

**Laminated        DEAE Cellulose / Nylon

*Fig. 18G*

2. Chemical /Personal Care

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 1 | LPO, FFA, and MDA | Fragrance Oil | MCE | diethylamine | Silica | | XO | MI | XO (Fe⁺ acidified) | | Spectral | |
| 2 | LPO after oxidative stress to predict shelf life | Oil Skincare Product | MCE | | | | | XO (Fe⁺ acidified) | | | Spectral | |
| 3 | LPO after UV exposure to determine SP or UVA | Biological matrix cells | MCE | | | | | XO (Fe⁺ acidified) | | | Spectral | Test to UVA |
| 4 | LPO after stress formulation | Formulation with or without stress; compare formulation Trolox | MCE | | | | | XO (Fe⁺ acidified) | | | Spectral | Test efficacy |
| 5 | LPO | Oxidative stressed cells digest | Versapor | | | | | XO (Fe⁺ acidified) | | | Spectral | Oxidative stress prediction mode of action |

LPO Reagent Only (rows 1)

Stress "toxicant" take sample before and after stress (rows 2–5)

Fig. 18H

3. Medical

| | Analytes | Typical Matrix | Membranes | | | | Reagents | | | | Detection Method | Comments |
|---|---|---|---|---|---|---|---|---|---|---|---|---|
| | | | $M_1$ | $M_2$ | $M_3$ | $M_4$ | $R_1$ | $R_2$ | $R_3$ | $R_4$ | | |
| 1. | VLDL LDL HDL | Serum | Membrane 300,000 MW trap VLDL | Membrane 100,000 MW cut-off trap LDL | Membrane 10,000 MW cut-off trap HDL | | quant VLDL cholesterol | LDL cholesterol | HDL cholesterol | | Spectral 510 | |
| 2. | LDL and oxidized LDL (LDL-) | Serum | 300,000 MW cut-off membrane | LDL-Trapped diethyl amine | | | LDL cholesterol detection | Rinse LDL-Cholesterol detection oxidized (Use cholesterol oxidase end substrate) | | | Spectral 510 | |
| 3. | LPO to determine AOS | Serum | MCE | | | | XO Fe⁺ Acidified | | | | Spectral | |
| 4. | LPO in serum to determine age | Serum | MCE | | | | XO Fe⁺ Acidified | | | | Spectral | |
| 5. | FFA | Serum | MCE | | | | XO | | | | Spectral | |

Fig. 18I

TABLE II

Key to Acronyms

| | |
|---|---|
| AOS | Antioxidant Status |
| ADP | Adenosine Triphosphate |
| AMP | Adenosine Monophosphate |
| ATP | Adenosine Triphosphate |
| DAO | Diamine Oxidase |
| FFA | Free Fatty Acids |
| HA | Histamine |
| HDL | High Density Lipoproteins |
| HRP | Horseradish Peroxidase |
| $I_2$ | Iodine Vapor |
| $I_3$ | Triodide Ion |
| IDA | Iminodi Acedtic Acid Membrane |
| LDL | Low Density Lipoproteins |
| LDL- | Oxidized Low Density Lipoproteins |
| LPO | Lipid Peroxides |
| Mab | Monoclonal Antibody |
| MCE | Mixed Cellulose Ester |
| MDA | Malonaldehydes |
| MI | Methylindole |
| SP | Sun Protector Factor |
| TBPB | Tetra Bromophenol Blue |
| TG | Triglyceride |
| TL | Total Lipids |
| SF | Sulfite |
| VLDL | Very Low Density Lipoproteins |
| XO | Xylenol Orange |

*Fig. 19*

TABLE III

Predictive Algorithms

| | | |
|---|---|---|
| 1. | Prediction of Olive Oil Adulteration using product FFA X Polyphenol<br>Please refer to row 29 of Appendix I. | FFA X Polyphenol – Numerical Scale<br>> 50 not adulterated<br>< 50 likely adulterated |
| 2. | Shelf Life Prediction based on MDA/LPO ratio | MDA/LPO is a scale 0 to 5<br>0-0.5    67% shelf life remains<br>0.5-1    33% shelf life remains<br>1-2    15% shelf life remains<br>>2    5% shelf life remains |
| 3. | Shelf Life Prediction based stress with peroxyl generator | % change related to shelf life<br>0-10%    >18 months<br>10-30%    12-18 months<br>30-50%    6-12 months<br>>50%    < 6 months |
| 4. | Freeze/Thaw Prediction using ratio Acidity/LPO | Ratio    Freeze/Thaw<br>0-0.2    one<br>0.2-0.4    two<br>0.4-0.6    three<br>0.6-0.8    four |
| 5. | Prediction of time to Myeotoxin contamination using LPO value<br>Please refer to row 33 of Appendix I. | LPO vs Time to Contamination (decreasing curve) |
| 6. | Prediction if food is Irradiated using FFA/LPO ratio | Food non-irradiated has expected FFA/LPO of <1<br><br>Food Irradiated increases FFA/LPO >1 |

Fig. 20

TABLE IV

| SHLEICHER & SCHUELL GmbH<br>P.O. Box 4, D37582, Dassel, Germany | APPLICATION<br>Removal of solid matter, proteins >.45 um |
|---|---|
| 1. Cellulose Acetate, 0.45 um's 25 mm discs - 23710 | Removal of solid matter, proteins |
| 2. Polyvinylidene Fluoride, 0.2 um's, 25 mm disks - 413005 | Antibody coating |
| 3. NA45 DEAE Cellulose Membrane, 0.45 um's, 25 mm discs - 23310 | Capture aldehydes |
| 4. NA45 DEAE Cellulose Membrane, 0.45 um's, 4x51/4 inches - 23430 | Capture of malonaldehyde, sulfites, sulfite-bound aldehydes |
| 5. Nylon, 0.45 um's, 25mm discs - 00130 | Removal of solid matter, proteins >.45 um |
| 6. Nylon, 0.2 um's, 25 mm discs - 00030 | Removal of solid matter, proteins > .2 um |
| 7. NL Polyamide | Capture organohalides |
| 8. PC Polycarbonate | Capture aldehydes |
| Poretics Corporation<br>111 A Lindbergh Ave., Livermore, CA 94550 | APPLICATION |
| 1. MicroPrep, PTFE, PP, NS, 0.2 um's, 13 mm - 97844 | Capture compounds having fatty acid chains lipid peroxides |
| 2. MicroSpin, Nylon, 0.45 um's, Micro-Cent. tubes - 97795 | Removal of solid matter, proteins |
| 3. Ultra-Spin, CTA, PP S, 10k MWCO, Micro-Cent Tubes - 97771 | Removal of solid matter, proteins |
| 4. Silver Membranes, 0.4 um's, 25mm - 51133 | Capture of volatiles |
| 5. Polycarbonate Membranes, 0.4 um's, 25 mm, PVP Free - 11030 | Capture aldehydes |
| 6. Polycarbonate Membranes, 0.4 um's, 25 mm, AOX - 11027 | Capture chlorinated molecules |
| 7. Polycarbonate Membranes, 0.45 um's 47 mm, Low extr. - 13035 | Capture aldehydes |
| 8. Polycarbonate Membranes, 0.2 um's, 8" x 10", PVP Free - 19416 | Capture aldehydes |
| MILLIPORE CORPORATION<br>80 Ashby Rd., Bedford, Ma 01730-2271 | APPLICATION |
| 1. Isopore, 0.1 um's, 25 mm discs - VCTP 025 00 | Removal of solid matter proteins |
| 2. Immobilon-CD, 0.45 um's, 25mm discs, Cationically charged (hydrophilic PVDF) - ICDM 025 00 | Removal of solid matter proteins |
| 3. Low water Extractable (TF) filters, 0.45 um's, 25 mm discs - HATF 025 00 | Removal of solid matter without binding organic molecules |
| 4. Hydrophilic Durapore, 0.45 um's, 25 mm discs - HVL-025 00 | Removal of solid matter proteins |
| 5. Immobilon (hydrophobic PVDF) high protein binding, 0.45 um's, 25 mm discs - ISEQ 025 00 | Capture aldehydes |
| 6. Isopore, HTTP (polycarbonate), 0.4 um's, 25 mm discs - HTTP 025 00 | Capture aldehydes |
| 7. Immobilon-P Transfer Membranes (PVDF), 0.45 um's, 15 cm x 15 cm - IPVH 151 50 | Coating with antibodies to capture or remove antibody specific compounds |
| 8. Immobilon Transfer Membranes (PVDF), 0.45 um's, 15 cm x 15 cm - ICDM 151 50 | Coating with antibodies to capture or remove antibody specific compounds |
| 9. Immobilon NC Pure, 0.22 um's, 15 cm x 15 cm - INCP 151 50 | Coating with antibodies to capture or remove antibody specific compounds |
| 10. Immobilon-NC (Surfactant free), 0.45 um's, 15 cm x 15 cm HATF 151 50 | Coating with antibodies to capture or remove antibody specific compounds |
| 11. MultiScreen - DEAE Anion Exchange Paper Opaque 96 well plates - MADE NOB 10 | Capture aldehydes |
| 12. MultiScreen - Phospho Cellulose Cation Exchange Paper Opaque 96 well plates MAPH NOB 10 | Bind lipid peroxides for capture |
| 13. SCX | MW Cutoffs timer polymers triglyceria |
| 14. Polysulfone | Amino acids, peptides proteins |
| 15. IGN-6 | Microbes |
| 16. ICE 450 | Bind nucleotides DNA |
| Sartorius<br>131 Heartland Blvd., Edgewood, NY 11717 | APPLICATION |
| 1. Sartoband S | Bind monoclonal antibodies, etc. |
| 2. Sartoband C | Endotoxin removal |
| 3. Sartoband Q | Separate proteins amines |
| 4. Sartoband D | DNA ADP ATP AMP |
| 5. Sartoband IDA | Metals; cations |
| Gelman/Pall<br>600 South Wagner Road, Ann Arbor, MI 48103-9019 | APPLICATIONS |
| 1. Versapor | Prefilter contaminants |
| 2. Ultrabind 05450 | Bind monoclonal antibodies, etc. |
| 3. Biodyne C | Separation proteins |
| 4. Biodyne B* | Endotoxins nucleotide separation |

*Fig. 21*

METHODS AND APPARATUS FOR DETERMINING ANALYTES IN VARIOUS MATRICES

RELATED APPLICATIONS

The present application is a continuation of U.S. patent application Ser. No. 09/183,157, filed Oct. 30, 1998, now abandoned, which is a continuation of U.S. patent application Ser. No. 09/058,238, filed Apr. 9, 1998, now abandoned, which is a continuation-in-part of U.S. patent application Ser. No. 08/723,636, filed Oct. 2, 1996, now U.S. Pat. No. 5,958,714, and which claims priority to United States Provisional Patent Application Serial No. 60/063,038, filed on Oct. 22, 1997, the entire disclosures of which are expressly incorporated herein by reference.

BACKGROUND OF THE INVENTION

Applicant's earlier-filed U.S. patent application Ser. No. 08/723,636, (sometimes referred to herebelow as the "parent application") describes certain methods and apparatus for determining the presence of one or more analytes in a complex matrix (i.e., a matrix which includes many diverse physical and/or chemical species, some or all of which may interfere with the intended analysis). The types of complex matrices in which applicant's analytical methods and apparatus may be used include foods, biological fluids (e.g. blood cerebrospinal fluid), cosmetic preparations, pharmaceutical preparations, etc.

The methods and apparatus described in parent application Ser. No. 08/723,636 include a test apparatus which generally comprise a) a first sample-receiving chamber, b) a second filtrate-receiving chamber fluidly connected to the first sample receiving chamber, and c) one or more membranes positioned between the first and second chambers. Initially, a quantity of the flowable, analyte-containing matrix is dispensed into the first chamber. The sample is then caused to flow through the membrane(s) which remove selected matter (particles, large molecules, secondary analytes, etc.) from the matrix, and the resultant filtrate is allowed to pass into the second chamber. After the filtrate has entered the second chamber, reagent(s) is/are added to such filtrate to facilitate qualitative or quantitative determination (spectrophotometric, visual, etc.) of primary analyte contained within the filtrate. In instances where multiple membranes have been employed, one or more of those membranes may have been used for the purpose of capturing one or more secondary analyte(s) which were present within the matrix along with the primary analyte. In those instances, the analyte-capturing membranes may subsequently be removed, and the secondary analyte(s) may then be eluted (e.g, released, washed) from those capture membranes and into secondary receiving chamber(s). Appropriate reagents are then added to the eluant(s) contained within the secondary receiving chamber(s) to facilitate qualitative or quantitative determination (e.g., spectrophotometric, visual) of the secondary analyte(s).

Applicant has now devised a number of improvements, additions and modifications to the test methods and apparatus described in parent application Ser. No. 08/723,636, and such improvements, additions and modifications are described and claimed in this continuation-in-part application.

SUMMARY OF THE INVENTION

The present invention provides apparatus, systems and methods for determining analytes in various types of samples (i.e., matrices).

In accordance with the invention, there are provided certain apparatus for non-electrophoretic testing of samples, such apparatus generally comprising a) one or more vessel(s) for receiving sample(s), b) one or more membrane modules which are positioned in alignment with the sample vessels(s) such that sample will pass through the membrane(s), and c) one or more filtrate receiving vessel(s) such that sample will pass through the membrane(s), and c) one or more filtrate receiving vessels positioned in alignment with the membrane modules, to receive filtrate which has passed through the membranes. Various numbers of membrane modules may be used, stacked upon one another, to remove particles, interferants or other unwanted matter from the sample and/or to capture certain analyte(s) for subsequent elution from the capture membrane and determination by suitable visual or analytical means. The test apparatus may include positive or negative pressure apparatus to create differential pressure within the apparatus for driving the samples through the membranes. Also, these apparatus may have a) specialized pressure equalization ports to ensure efficient and complete processing of all samples, b) selective engagement apparatus for engaging and disengaging the membrane modules and other components to/from one another and to form substantially air tight seals therebetween when assembled, c) specific configurations to allow the membrane modules and other components to nest or register with one another in a manner which facilitates proper orientation and functional positioning of all components, d) specific construction and mounting of membranes to deter tearing or rupture of the membranes during operation, and to maximize the functional surface area of the membrane(s), and (e) structural attributes which hold multiple membranes in close-spaced, stacked relation to each other during operation.

Further in accordance with the invention, there are provided systems and test kits as listed in TABLE I. The systems and test kits comprise specific membrane(s), preparation reagent(s), eluant(s) (if necessary) and analytical reagent(s) for use in connection with the above-summarized apparatus, in determining specific analyte(s) in specific types of matrices.

Still further in accordance with the invention, there are provided certain novel chemical tests for histamine, sulfite and/or bisulfite, free fatty acids, and lipid peroxides, as detailed herein and shown in TABLE I.

Further aspects and particulars of the present invention will become apparent to those of skill in the art upon reading and understanding the following detailed description of the preferred embodiments and examples and consideration of the accompanying drawings.

BRIEF DESCRIPTION OF THE DRAWINGS AND APPENDICES

A. Figures

FIG. 12 is an exploded, side elevational view of a fourth embodiment of a test apparatus of the present invention.

FIG. 12a is a bottom plan view of one of the membrane modules of the apparatus of FIG. 12.

FIG. 13a is an enlarged, cut-away, perspective view of a single membrane cell of the alternative membrane module of FIG. 13.

FIG. 15a is a perspective view of one component of a fifth embodiment of a test apparatus of the present invention.

FIG. 15b shows the component of FIG. 15a from an angle which allows one to see the test tube-receiving cavities formed within that component.

FIG. 15c is a perspective view of another component of the fifth embodiment of the test apparatus shown in FIGS. 15a–15b.

FIG. 15d showes the component of FIG. 15c from an angle which allows one to see the underside of that component.

FIG. 15e shows yet another component of the fifth embodiment of the test apparatus shown in FIGS. 15a–15d.

FIG. 16 is a perspective view of a multi-use vacuum base apparatus which is useable in conjunction with various ones of the test apparatus of the present invention.

FIG. 17 is a schematic showing of a dipstick testing apparatus of the present invention.

FIGS. 18A–18I depicts TABLE I listing a number of preferred test methods/kits of the present invention.

FIG. 19 shows TABLE II which is a key to the acronyms used to designate specific membranes, reagents, and substances in TABLE I of FIGS. 18A–18I.

FIG. 20 shows TABLE III listing commercially available membranes useable in the test methods/kits of TABLE I.

Figure 4:
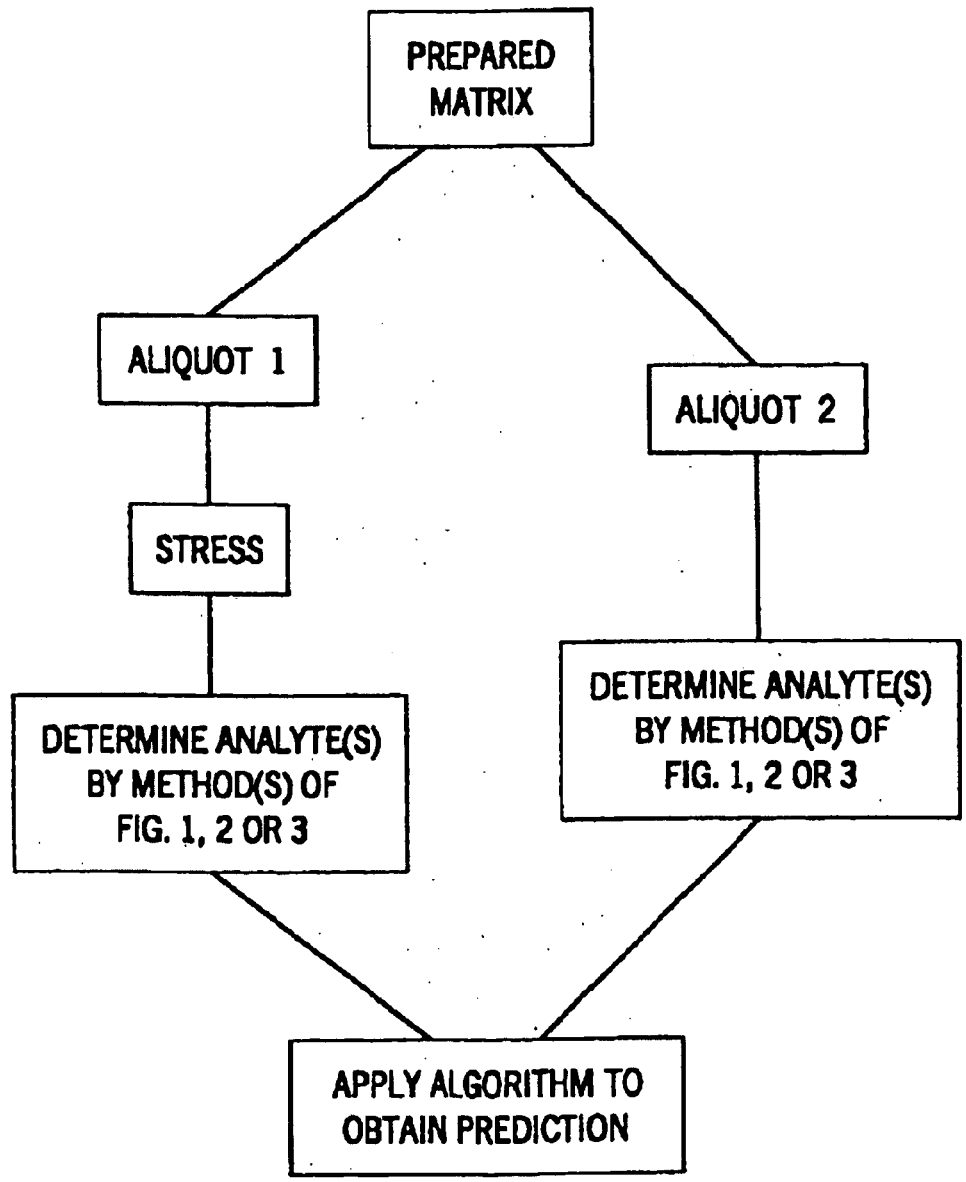
FIG. 4 is a flow diagram of a general method for utilizing one or more of the analytical methods of FIGS. 1, 2 and/or 3 to obtain a prediction as to the shelf life or other parameter of the sample matrix.
Figure 5:
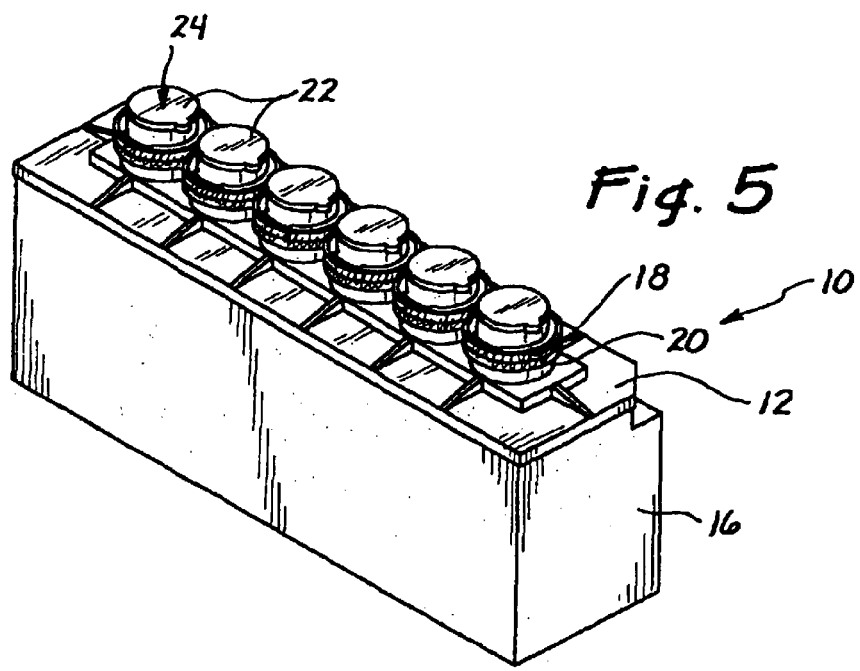
FIG. 5 is a perspective view of a first embodiment of a test apparatus of the present invention.

FIG. 21 shows TABLE IV listing algorithms which are useable in conjunction with certain test kit & methods of the present invention to predict or discern certain parameters, such as shelf life, presence of contaminants, potential for oxidative degradation, etc, in accordance with the general method diagram of FIG. 4.

DETAILED DESCRIPTION OF CERTAIN EMBODIMENTS

Throughout the following detailed description, the preferred embodiments and examples referred to should be considered as exemplars, rather than limitations on the apparatus and methods of the present invention. Although applicant has described certain exemplary embodiments herebelow, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

A. General Methodology

The methods of the present invention range in complexity from a basic method whereby the presence of a single analyte may be qualitatively determined to a complex method whereby a plurality of different analytes may be quantitatively determined from a single analytical sample.

i. General Method for Determining a Single Analyte

Figure 1:
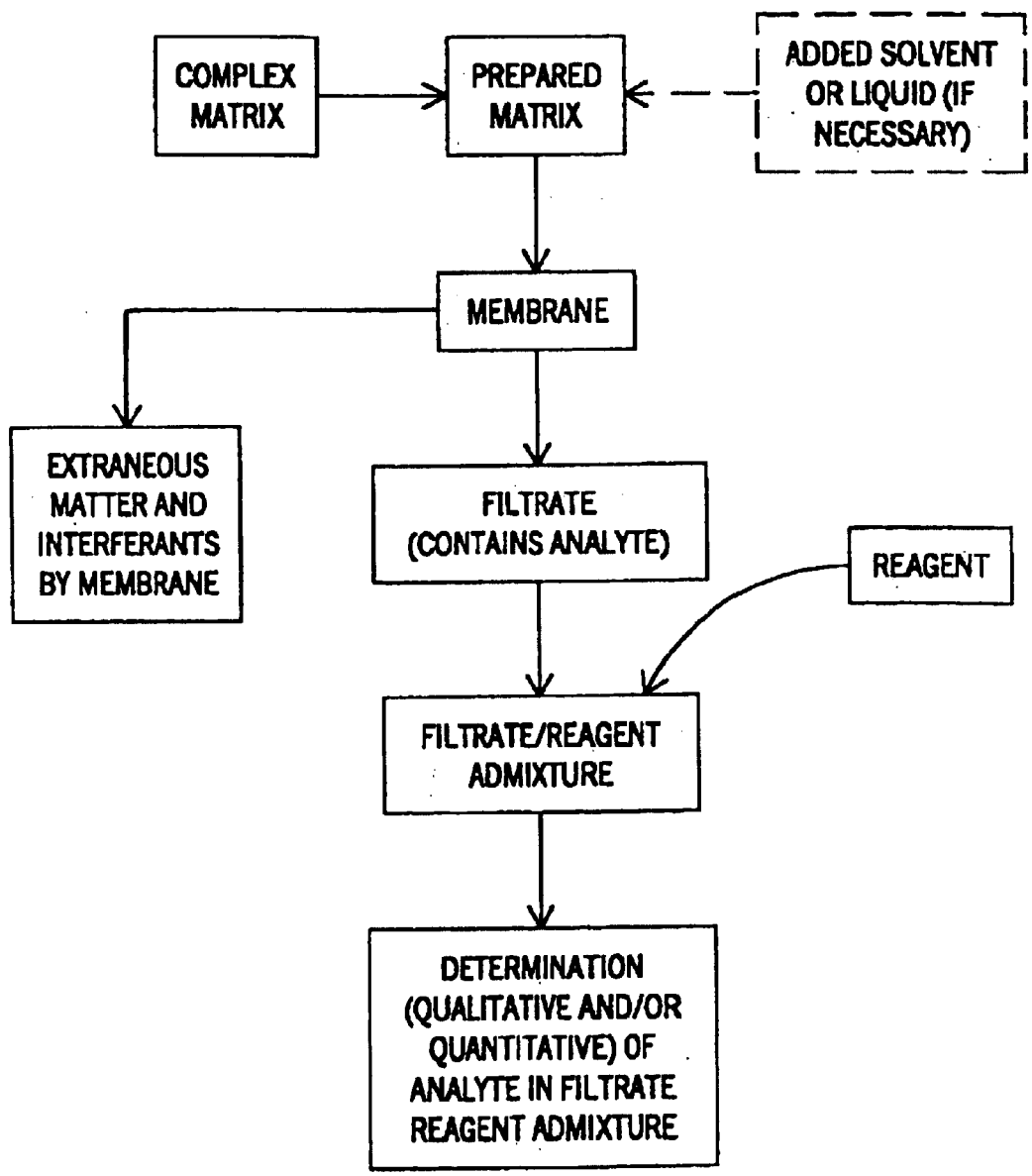
FIG. 1 is a flow diagram of a general method of the present invention, for detecting a single analyte.

FIG. 1 shows a flow diagram of a basic method of the present invention wherein a single analyte may be qualitatively and/or quantitatively determined within a complex matrix (i.e., a matrix which contains one or more materials other than the analyte).

Initially, the complex matrix is prepared and, if necessary, is combined with added solvent or liquid to form a prepared matrix for subsequent processing. In instances where the complex matrix is a solid material (e.g., food) it will typically be necessary to grind or chop the complex matrix and to add a solvent, digestant, or other carrier liquid such that the "prepared matrix" will be in the form of a slurry or suspension.

For many applications of the invention, and in particular those wherein it is desired to detect specific analytes present in solid matrices such as foods, a digester/stabilizer solution including enzyme(s) and/or stabilizer(s) and/or chelator(s) may be added to the matrix during the preparation step to extract or dissolve the desired analyte(s). Examples of digesters which may be included in such solution include lipase enzymes and protease enzymes, and certain proprietary digester/stabilizer formulations as described in parent application Ser. No. 08/723,636. Examples of chelators which may be included in such solution include EDTA. One particular digester/stabilizer solution which may be utilized has the following formulation:

| | |
|---|---|
| Isopropanol | 70% by weight |
| Tween 20 | 2.0% by weight |
| EDTA | 0.1% by weight |
| Mannitol | 10 mM |

After the matrix sample has been prepared to a flowable state, it is passed through a membrane which removes or retains extraneous matter (e.g., solid particles or interfering substances such as proteins) while allowing a filtrate, which contains the analyte, to pass therethrough. In many instances, the membrane will be in the form of a microporous cellulose or polymer film having a desired pore size (e.g., 0.2–0.6 microns, and typically about 0.45 microns) which will filter out large proteins and relatively large solid particles while allowing relatively small solid particles and the accompanying liquid containing the analyte to pass therethrough. One example of a membrane which may be used for this purpose is a membrane formed of mixed cellulose ester film having 0.45 micron pores formed therein (e.g., ME-25 Membrane, Schleicher & Schuell GmbH, P.O. Box 4, D37582, Dassel, Germany).

The analyte-containing filtrate which passes through the membrane is subsequently mixed with one or more reagents to provide a filtrate/reagent admixture from which the desired qualitative and/or quantitative determination of the analyte may be performed.

Thereafter, the filtrate/reagent admixture is subjected to the desired analytical or measurement techniques to provide the intended qualitative and/or quantitative determination of the analyte. In some instances, this determination of the analyte may be made by a simple chemical test whereby a visual indicator (e.g., a color change) will indicate the presence and/or concentration of the analyte. In other instances, the determination of the analyte will be carried out by one or more analytical instruments, such as a calorimeter, spectrophotometer, optical densitometer, fluorometer, etc.

Thus, the general method illustrated in the flow diagram of FIG. 1 provides a means for qualitatively and/or quantitatively measuring an analyte which is present within a complex matrix.

ii. General Method for Detecting Multiple Analytes

Figure 2:
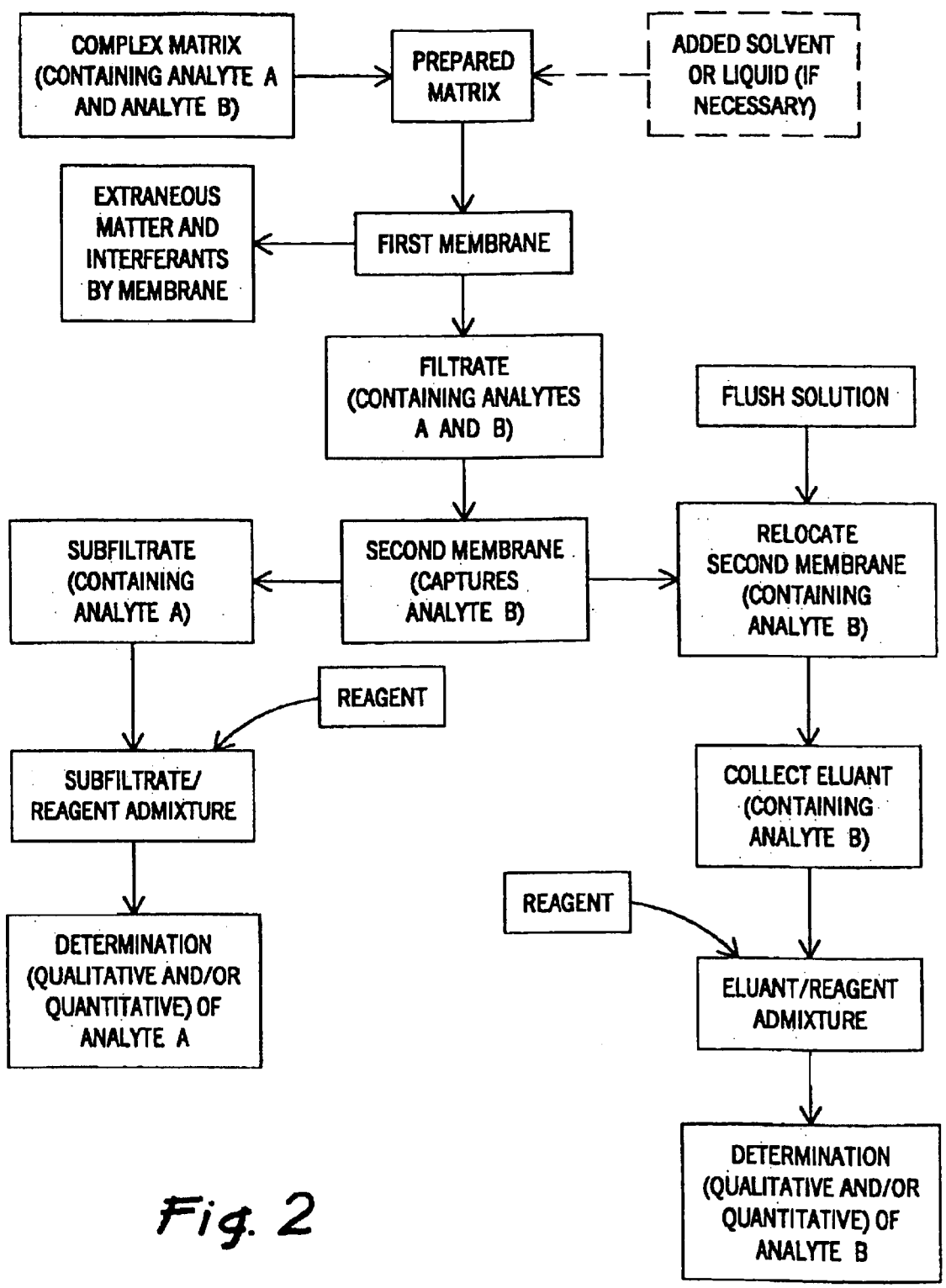
FIG. 2 is a flow diagram of a general method of the present invention, for detecting multiple analytes.

FIG. 2 shows a more elaborate general method of the present invention wherein it is desired to analyze two (2) separate analytes present within a complex matrix. The complex matrix in this example may be the same as that described hereabove with respect to FIG. 1 (e.g., food), and the method of preparing the complex matrix and the optional addition of solvent or liquid may be carried out in the same manner.

Thereafter, the prepared matrix is passed through a first membrane which retains or removes extraneous matter while allowing a filtrate, which contains both analytes a and b, to pass therethrough. As described hereabove, the first membrane may comprise a microporous membrane having known pore size so as to remove particles of solid matter which are larger than the membrane pore size, while allowing smaller particles of solid matter and the accompanying liquid containing Analytes A and B, to pass therethrough. As in the example of FIG. 1, one such membrane may be formed of mixed cellulose ester film (e.g., ME-25 Membrane, Schleicher & Schuell GmbH, P.O. Box 4, D37582, Dassel, Germany).

Thereafter, the filtrate which has passed through the first membrane will be subsequently passed through a second membrane. This second membrane is adapted to capture and hold Analyte B, while allowing a sub-filtrate containing Analyte A to pass therethrough. In this manner, the second membrane serves to separate and remove Analyte B from Analyte A.

The Analyte A-containing sub-filtrate which has passed through the second membrane will be thereafter combined with a reagent to provide a sub-filtrate/reagent admixture from which qualitative and/or quantitative determination of Analyte A may be performed.

Thereafter, the desired qualitative and/or quantitative determination of Analyte A is performed on the sub-filtrate/reagent admixture in the same manner as described hereabove with respect to FIG. 1.

The second membrane, which contains Analyte B, may be removed or relocated and a flush solution, capable of releasing and carrying Analyte B from the second membrane, will be passed therethrough. Such passage of the flush solution through the second membrane will provide an eluant of known volume, which contains Analyte B.

Thereafter, the eluant containing Analyte B is combined with a reagent to provide an eluant/reagent admixture from which Analyte B may be qualitatively and/or quantitatively determined.

Thereafter, the qualitative and/or quantitative determination of Analyte B is performed on the eluant/reagent admixture in the manner described hereabove with respect to FIG. 1. Thus, the example shown in FIG. 2 provides a method whereby two separate analytes may be qualitatively and/or quantitatively determined in a complex matrix.

It will be appreciated that, although FIG. 2 provides an example wherein only two analytes (e.g., Analyte A and Analyte B) are determined, it will be possible to determine any desired number of analytes in accordance with the present invention by providing additional secondary membranes in series with the "second membrane" shown in FIG. 2, so as to capture and collect each of the desired analytes. Thereafter, flush solutions may be passed through each of these secondary membranes to provide eluants containing each of the individual analytes. Those eluants may then be combined with reagents and subjected to the desired qualitative and/or quantitative determinations for the desired analytes.

iii. General Method for Detecting Analyte(s)

Present at Low Concentrations

Figure 3:
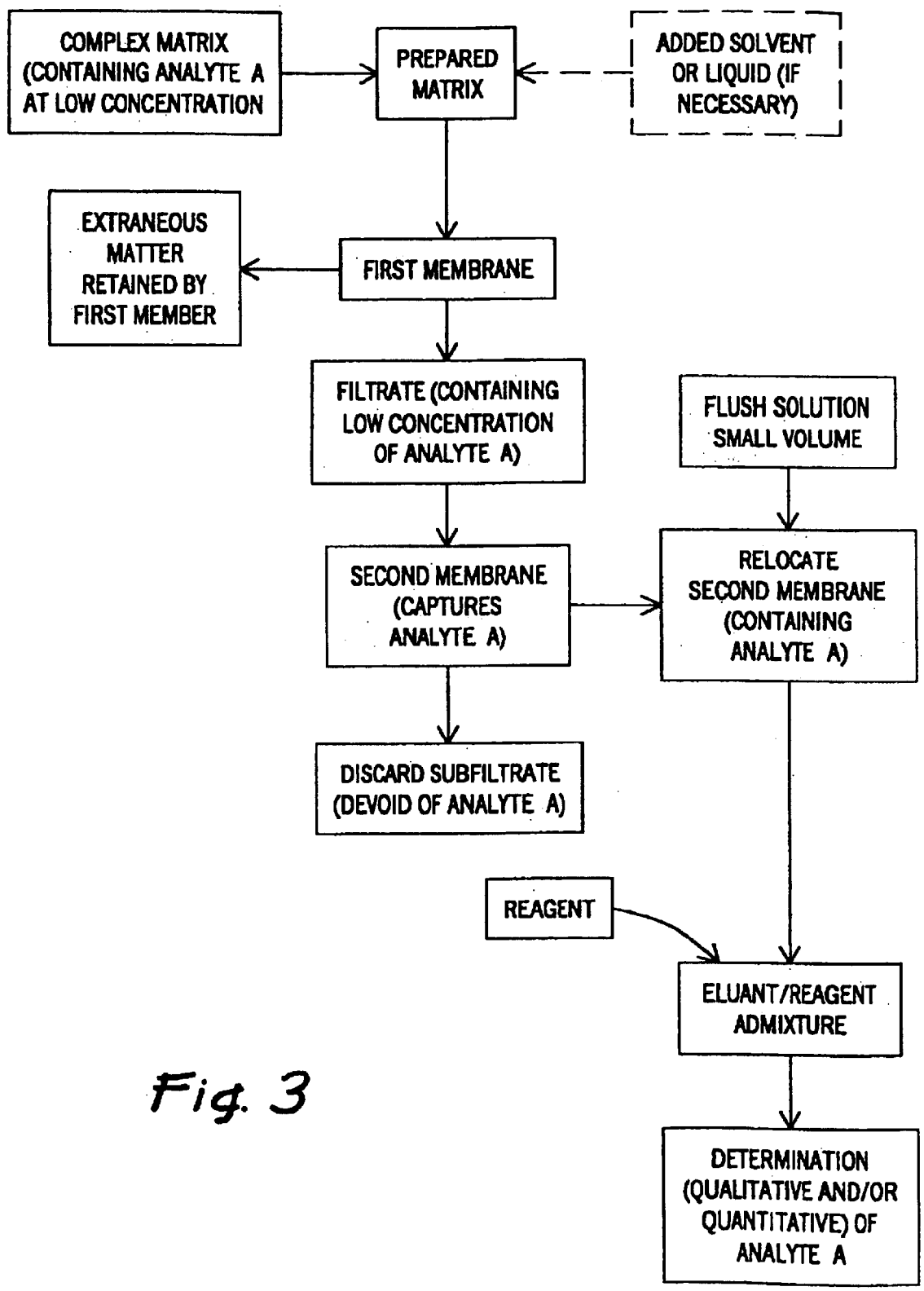
FIG. 3 is a flow diagram of a general method of the present invention, for detecting an analyte which is present at low (e.g., sub-detectable) concentration in a complex matrix.

FIG. 3 shows another example of a method of the present invention wherein it is desired to qualitatively or quantitatively determine the presence of a single analyte, which is present in a complex matrix at a concentration below the detection limits for the analytical procedure to be used.

In the example shown in FIG. 3, the complex matrix is prepared and optionally combined with solvent or liquid in the same manner as described hereabove with respect to FIGS. 1 and 2.

Thereafter, the prepared matrix is passed through a first membrane which will retain extraneous matter, while allowing a filtrate containing the Analyte A to pass therethrough. This first membrane may be the same type of first membrane described hereabove with respect to FIGS. 1 and 2.

Thereafter, the filtrate, which contains Analyte A, is passed through a second membrane. The second membrane is operative to capture and hold Analyte A, while allowing the remaining fraction(s) of the filtrate to pass therethrough as a sub-filtrate, which is subsequently discarded.

The second membrane, which contains Analyte A, is then relocated and positioned over a well or containment vessel, and a known volume of flush solution is passed therethrough. The volume of flush solution which is passed through the second membrane will be less than the volume of filtrate which had previously been passed through the first membrane. Passage of this flush solution through the second membrane will release and carry Analyte A from the second membrane. In this manner, there is provided an eluant/reagent admixture wherein Analyte A is contained at a concentration which is higher that the original concentration of the Analyte A in the filtrate which passed through the first membrane. Thus, Analyte A is now present in the eluant at a concentration which is high enough to be detected or measured by the desired analytical procedure or method.

Accordingly, the desired qualitative and/or quantitative determination of Analyte A is performed on the eluant/reagent admixture, in the manner described hereabove with respect to FIGS. 1 and 2.

Thereafter, well known mathematical principles may be utilized to calculate the concentration at which Analyte A was present in the original complex matrix, although Analyte A was subsequently concentrated into the eluant/reagent admixture at higher concentrations capable of being detected or determined by the desired analytical procedure.

iv. General Methodology for Predicting Changes in a Sample

FIG. 4 shows a bock diagram of a general method whereby the test methods and apparatus of the present invention may be used to predict the occurrence of certain changes (e.g., oxidation, other degradation, spoilage) which a sample is likely to undergo within a given time period. These techniques may be used as predictors of shelf life, propensity for oxidative degradation, presence of contaminants, etc. Specific examples of this general method are set forth in detail herebelow.

In these predictive procedures, the sample is initially prepared (e.g, ground, chopped, macerated, digested, dissolved, etc) as necessary and is optionally combined with a solvent or liquid in the same manner as described hereabove with respect to FIGS. 1, 2 and 3.

Thereafter, aliquots of the prepared sample are placed in separate vessels. One sample is subjected to a stress (e.g., heat, light, air, etc.) which is known to promote the particular change which is sought to be predicted. (e.g., oxidation, degradation, etc.)

Thereafter, one or more analytes indicative of the change sought to be predicted, are determined in the stressed and un-stressed aliquots, using one or more of the general methods shown in FIGS. 1, 2 and 3 and generally described hereabove.

The results of the analyte determinations are then processed by way of an algorithm or formula, to arrive at the desired prediction as to whether the sample will undergo the particular change (e.g., oxidation, degradation, etc.) within a particular time period. Examples of specific algorithms which are useable in this regard are shown in the table of Appendix IV.

In this manner, the test kits/methods of the present invention may be adapted and used to provide predictions of shelf life, stability, color longevity, etc.

B. Preferred Apparatus

FIGS. 5–16 show various embodiments of apparatus which are useable to perform the analytical methods of applicant's invention. Set forth herebelow are detailed descriptions of each of the exemplary embodiments shown in the drawings.

i. First Embodiment of Test Apparatus

Referring to FIGS. 4–9, the first embodiment of the test apparatus 10 generally comprises the following components: a) a vacuum base 16, b) a test tube rack 14, c) a cover 12, d) membrane module(s) 18, 20, and e) lids 22. As described in the following paragraphs, these components of the apparatus 10 are configured and constructed to be assembled and disassembled in a particular manner to facilitate the performance of analytical tests in accordance with applicant's above-described methodologies.

The vacuum base 16 comprises a housing having a cavity 17 formed therein and opening though the top of the base 16. A vacuum port 32 is formed in the base 16 to permit a vacuum line to be attached to the base for the purpose of drawing a partial vacuum within the cavity 17. A seal 30, such as an oval-shaped o-ring, is mounted about the upper opening of the cavity 17, as shown.

The test tube rack 14 has a plurality of test-tube receiving slots into which test tubes 15 are inserted. The test tube rack 14 with the test tubes 15 inserted therein is then inserted downwardly into the cavity 17 of the base, as can be appreciated from the exploded view of FIG. 5. Finger passage notches 34 are formed on either side of the cavity 17 to permit the users fingers to pass freely into the cavity 17 on either side of the test tube rack 14 when inserting or removing the test tube rack 14.

The cover 12 comprises a generally flat member having a series of sample ports 13 formed therein. The sample ports are located and configured such that they will be in direct alignment with the mouths of the test tubes 15, when the cover 12 and test tube rack 14 are properly mounted within the apparatus 10. Also, the sample ports 13 have rims 28 which are configured to receive and hold one or more membrane modules 18, 10 thereon.

The membrane modules 18, 20 are of two (2) basic types—primary membrane modules 20 and secondary membrane modules 18. The primary membrane module 20 has a sample-receiving well 21 formed therein and incorporates a membrane 52 a which typically serves to remove particles, large molecules or other unwanted matter from the matrix as the sample passes therethrough. The secondary membrane module(s) 18 incorporate membrane(s) 52b which typically serve either to a) capture secondary analyte(s) for subsequent analysis, b) capture a primary analyte which is present in the matrix at low (e.g., sub-detectible) concentrations to permit such analyte to be subsequently concentrated and determined (i.e., qualitatively detected or quantitatively analyzed), or c) remove specific contaminants (e.g., metals) which were not removed by the first membrane and which require a different type of membrane to be captured and removed. Thus, the primary membrane module 20 is used in most if not all applications of the apparatus 10, while the secondary membrane module(s) 18 are used only when a) two or more analytes are to be determined or b) the primary analyte is present in the matrix in low concentrations and must be subsequently concentrated to permit its determination.

As shown specifically in FIGS. 5, 6, 7 and 8, the primary and secondary membrane modules 20, 18 are formed partially of a hard polymer HP such as polypropylene, polystyrene or polyethylene and partially of an elastomer EM such as a natural or synthetic rubber or similar material. This dual resin construction may be accomplished by co-molding techniques whereby the first (i.e., hard) resin is shot into the mold and, thereafter, the second (i.e., elastomeric) material is shot into the same mode so as to become adherent upon or fused with the first (i.e., hard) resin. In this manner the preferred two-material construction described above, can be accomplished in a single mold with minimal manual operation and handling. Alternatively, this dual resin construction may be accomplished by a two (2) step "over molding" process which is known in the art of injection molding.

The elastomeric EM portions of the membrane modules 20, 18 are configured and located to abut against the adjacent membrane module(s) 20, 18 and/or against the adjacent sample port rim 28, to effect a substantially air-tight seal therebetween. The sealing contact between the membrane modules 20, 18 and the sample port rims 28 may be facilitated by the interaction of connector members 40, 42 formed thereon. In this regard, the rims 28 of each sample port 13, and of each secondary membrane module 18, are provided with first connector members such as projections 40. Each primary and secondary membrane module 20, 18 is also provided with corresponding second connector members such as slots 42, into which the first connector members 40 will insert and engage to thereby hold the primary and secondary membrane modules 20, 18 in stacked, sealing contact upon each sample port 13, as shown.

Figure 9:
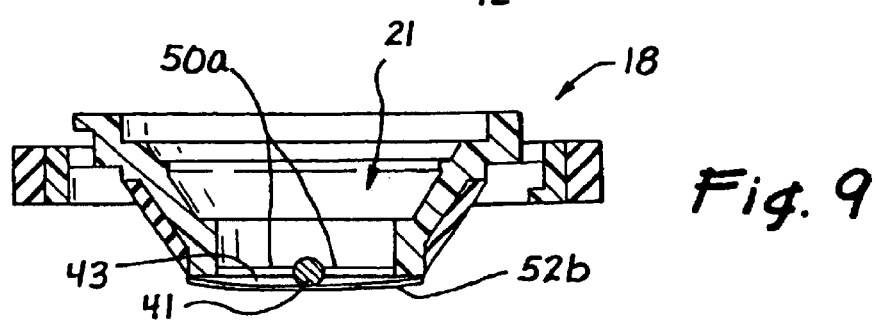
FIG. 9 is a transverse sectional view of the secondary membrane module of FIG. 7.

The number of secondary membrane modules 18 mounted on each sample port 13 may vary (i.e. from zero upward) depending on the number of analytes to be determined. In this regard, the primary membrane module 20 is typically located on the top of the stack such that the flowing matrix will pass through the membrane 52a of the primary membrane module before passing through the membranes 50b of the secondary membrane module(s) 18. Because different types of membranes 52a, 52b are used to perform different tests, the primary and secondary membrane modules 20, 18 may be color coded or otherwise marked for easy identification of the type of membrane 52a, 52b present hereon. The membrane 52a, 52b or each membrane module 20, 18 is attached (e.g., by heat fusion, adhesive or other acceptable means) to membrane support structure such as a ring, flange or cross-members 50a, 50b formed within each membrane module 20, 18. A central attachment projection 41 extends downwardly from support cross-members 50a, 50b, and such projection 41 is fused or affixed to the membrane 52a, 52b of that membrane module 18, 20. In this manner, as shown in FIG. 9, the center of each membrane 52a, 52b is suspended from the attachment projection 41 and the membrane 52a, 52b is thereby deterred from rupturing or blowing out as the flowable sample is being drawn downwardly through the membrane 52a, 52b. At the same time, however, the membrane will remain substantially unattached to the undersides of the cross-members 50a, 50b and flowable sample is permitted to flow into and occupy a gap 43 which exists between the membrane 52a, 52b and the adjacent cross-members 50a, 50b. This serves to avoid the diminution in effective surface area of the membrane 50a, 50b as would occur if the membranes 52a, 52b were fused or affixed directly to the cross-members 50a, 50b. Such maximization of the effective area of the membrane 52a, 52b will serve to promote rapid flow of filtrate (or sub-filtrate) through each membrane 52a, 52b.

The lids 22 are mountable in sealing contact on the rim 20 or each primary membrane module 20. A limited air inflow port 24 is formed in each lid 22 to permit a controlled amount of make-up air to pass into each sample-receiving well. These controlled flow ports 24 may comprise holes with segments of tubing inserted therewithin. The size of the lumen of each such segment of tubing may be selected to provide the desired limitation or constriction on the flow of air which enters each sample-receiving well 21. In the particular embodiment shown, which is designed for simultaneous processing of six (6) samples, the inflow rate through each flow port 24 is preferably no greater than ⅚ the capacity of the vacuum pump used to pull negative pressure within the apparatus 10, as described more fully below. In this manner, the provision of these controlled flow ports 24 will ensure that, even when the liquid within five (5) of the six (6) sample-receiving wells 21 has been fully drawn through the membranes 52a, 52b and into the test tubes 15, the amount of make-up air received through those five (5) depleted sample-receiving wells 21 will not be so large as to completely nullify the capability of the vacuum pump to pull adequate negative pressure to draw the remaining liquid through the filter and/or membranes of the remaining sixth sample-receiving well 21.

It will be appreciated that although the apparatus 10 shown in the attached drawing is designed for simultaneous processing of six (6) samples, the apparatus 10 may alternatively be designed to process any desired number of samples. However, since this particular embodiment of the apparatus requires handling and mounting of the individual membrane modules 20, 18 and lids 22, it will typically be used for relatively small numbers of samples (e.g., less than 24). Another embodiment 10a (described herebelow and shown in FIG. 7) is more suited for simultaneous processing of large numbers (e.g., more than 24) samples.

In operation of the first embodiment of the apparatus 10 shown in FIGS. 5–9, a suction or vacuum tube is connected to the vacuum port 32 of the base 16, and a test tube rack 14 containing clean test tubes 15 is inserted into the cavity 17 of the base 16. Thereafter, the desired primary and secondary membrane modules 20, 18 are mounted in firm sealing engagement on the sample ports 13, and the cover 12 is mounted in firm sealing contact on the base 16. In some applications clamps, rubber bands, screws, or other connector apparatus (not shown) may be applied to hold the cover 12 in firm sealing contact with the seal member 30 of the base 16. In other applications, the cover 12 may be constructed to snap fit or otherwise mount in sealing contact with the seal member 30 without the use of such connector apparatus.

After the cover 12 has been mounted on the base 16, quantities of the flowable sample(s) are dispensed into the sample-receiving cavity 21 of each primary membrane module 20, and the lids 22 are applied. Thereafter, the vacuum source is actuated and negative pressure is formed within the cavity 17 of the base 16. This negative pressure within the apparatus 10 causes the quantities flowable sample(s) dispensed into the sample-receiving cavities 21 to flow downwardly through the first membrane 52a, through and secondary membrane(s) 52(b), and the resultant filtrate then collects within the test tubes 15.

Thereafter, the cover 12 is removed, and the test tube rack 14 (with the filtrate-containing test tubes 15) is removed. The desired reagent (s) is/are then mixed with the filtrate contained in the test tubes 15, and the reagent-filtrate admixture is then subjected to the appropriate analytical technique (e.g., spectrophotometry, visual comparison to color chart or color wheel, etc.) to qualitatively or quantitatively determine the first analyte in the filtrate.

Thereafter, clean test tubes 15 may be inserted into the rack 14 and the rack 14 replaced in the cavity 17 of the base 16. The first membrane modules 20 are removed and discarded. The cover 12, having the second membrane modules 18 mounted on its sample ports 13 is then once again mounted in sealing contact upon the base 16. A quantity of an agent or eluant capable of releasing or eluting the second analyte from the second membrane 52b, is then dispensed into the release agent receiving cavities 19 of the secondary membrane modules 18, and the lids 22 are placed in sealing contact upon the second membrane modules 18. The vacuum pump is then used to once again draw negative pressure within the apparatus 10, thereby causing the eluant to flow downwardly through the second membranes 52b and thereby eluting the second analyte from the second membranes 52b. The eluant/second analyte mixture is then received within the clean test tubes 15. The vacuum pump is turned off, the test tube rack 14 is removed, and appropriate reagent(s) are then mixed with the eluant/second analyte contained within the test tubes 15. The desired reagent(s) is/are then mixed with the eluant/second analyte contained in the test tubes 15, and the eluant/second analyte/reagent admixture is then subjected to the appropriate analytical technique (e.g., spectrophotometry, visual comparison to color chart or color wheel, etc.) to qualitatively or quantitatively determine the second analyte in the eluant.

It will be appreciated that this process may then be repeated for each additional secondary membrane module 20 used, to determine N additional analytes within the samples.

ii. Second Embodiment of Test Apparatus

Figure 10:
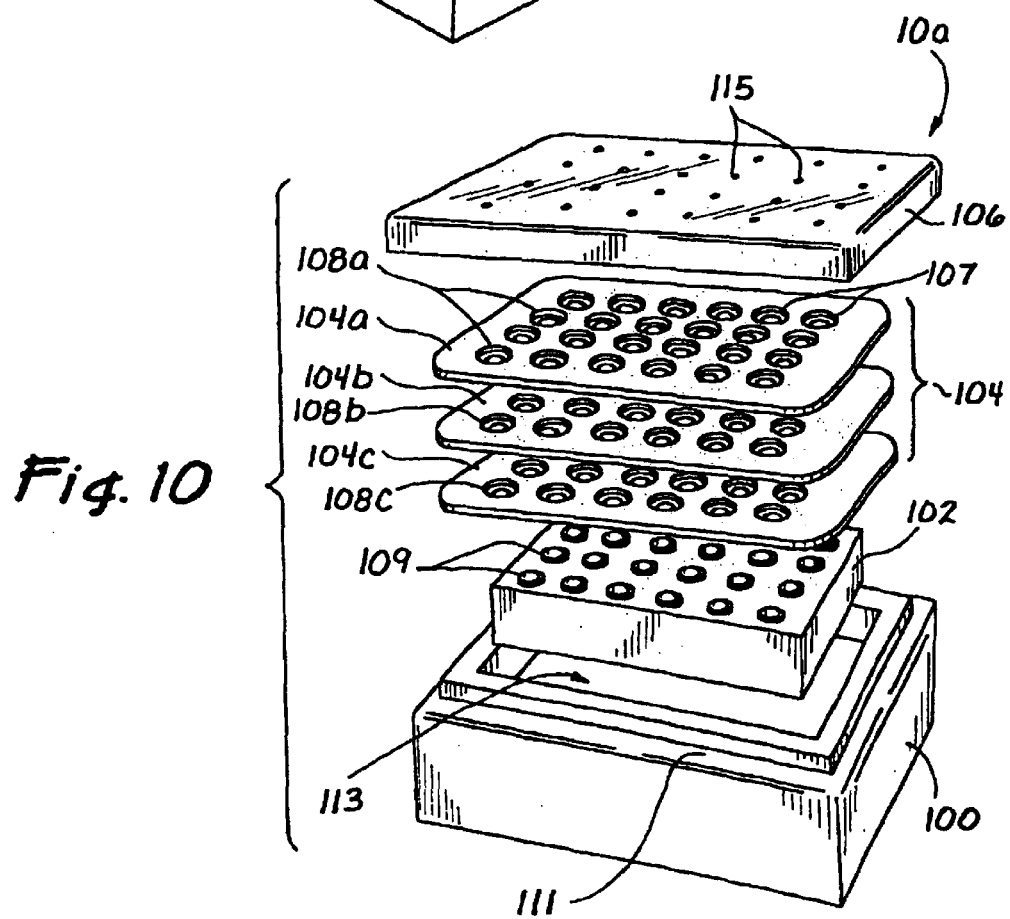
FIG. 10 is an exploded perspective view of a second embodiment of a test apparatus of the present invention.

Referring to FIG. 10 a second embodiment of the test apparatus 10a generally comprises a) a vacuum base 100, b) a receiving unit 102 having 24 filtrate-receiving wells 109 formed therein, c) plate-type membrane modules 104a, 104b, 104c, each having multiple (e.g. twenty-four(24)) cavities with bottom openings and membranes 108a, 108b, or 108c mounted transversely within such bottom openings, and d) a cover 106 having 24 individual air inlet ports 115 formed therein.

The receiving unit 102 is inserted into the base 100, and the membrane modules 104a, 104b, 104c are stacked upon the receiving unit such that the individual cavities and membranes of each membrane module 104 are in direct alignment with each other and with the filtrate-receiving wells 109 of the receiving unit. Quantities of sample are initially deposited in sample-receiving wells 107 formed on the upper surface of the first membrane module 104a and the lid 106 is placed in sealing contact with the rim 111 of the base 100, and each individual air inlet port 115 formed in the lid 106 is positioned to provide an air inlet into one of the sample-receiving wells 107 of the first (upper) membrane module 104a. Thereafter, a source of negative pressure is connected to a port (not shown) formed in the base so as to create negative pressure within the cavity 113 of the base 100. This negative pressure causes each sample to be drawn downwardly through the membranes 108a, 108b and 108c positioned under that receiving well 107, and the resultant filtrate to be received in the filtrate-receiving well 109 positioned under those membranes. In this manner, this second embodiment of the test apparatus 10a may be used to simultaneously process up to 24 separate samples.

Typically, the membranes 108a of the first membrane module 104a are for the purpose of filtering out or removing interferants, particles or other unwanted matter while the membranes of any secondary membrane modules 104b, 104c are for capturing analytes for subsequent concentration and/or analysis. Accordingly, after the initial filtrate has been received in the filtrate receiving wells 109, the vacuum source is terminated or disconnected, differential pressure within the apparatus 10a is allowed to equalize to a point where removal of the lid 115 will not cause substantial upward buldging or rupture of the membranes 108a, 108b, 108c, and the lid 115 is removed. All of the membrane modules 104 are then removed and the first membrane module 104a with the captured particles, interferants and/or other unwanted matter is discarded.

Thereafter, the receiving unit 102 is removed and appropriate reagent(s) are added to the filtrate contained within the filtrate receiving wells 109 to provide a filtrate-reagent admixture from which a desired first analyte (Analyte A) may be qualitatively or quantitatively determined.

In applications where secondary plate-type membrane modules 104b and/or 104c are used, such secondary membrane modules 104b, 104c will typically have captured secondary analyte(s) (Analytes B, C, etc . . . ) which are to be subsequently released from the membranes 108b, 108c and thereafter concentrated and/or determined. In furtherance of this, a clean receiving unit 102 may be inserted into the cavity 113 of the base 100, and one of the secondary membrane modules 104b or 104c is then positioned on top of the new receiving unit 102 such that each membrane 108b or 108c is positioned over a receiving well 109. A known volume of flush solution or eluant is then placed in the cavity above each membrane 108b or 108c, and the lid 115 is replaced such that it is in sealing contact with the base 100 and the air inlet openings 115 are in alignment with each cavity on the membrane module 104b or 104c. The vacuum source is then reenergized or reconnected to the base to cause a differential pressure to be once again established within the apparatus 10a. In this manner the flush solution or eluant is drawn downwardly through the membranes 108b or 108c so as to extract or release the captured analyte(s) from the membranes 108b or 108c. An eluant/analyte mixture is thus received within each receiving well, and the above described procedure is repeated to qualitatively or quantitatively determine that analyte in the eluant/analyte mixture within each receiving well.

The same procedure is then repeated for each secondary membrane module 104b, 104c until all analytes have been determined.

Modified Plate-type Membrane Modules

Figure 8:
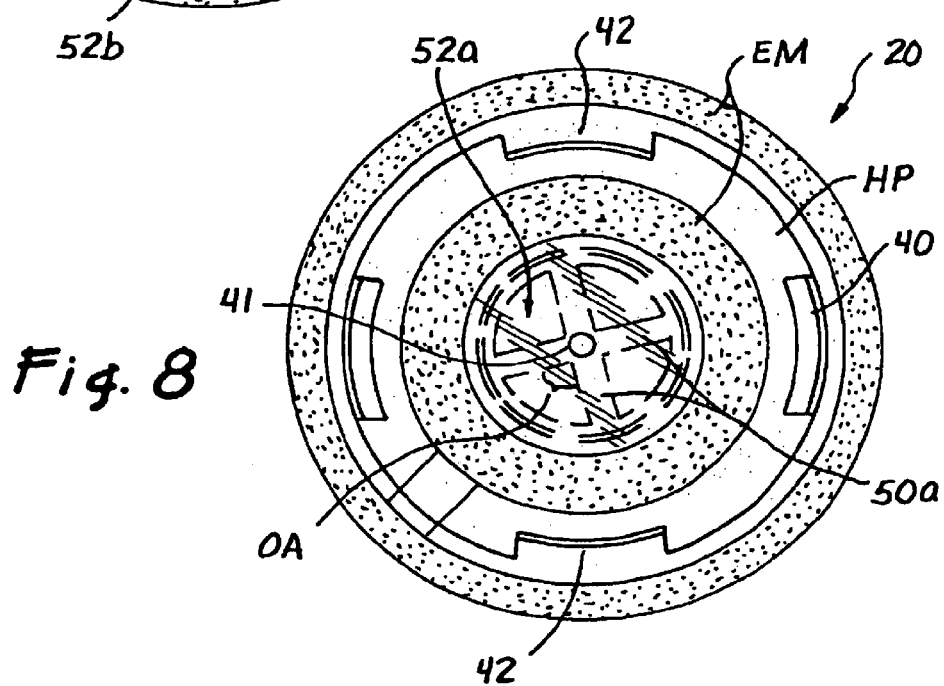
FIG. 8 is a top plan view of a primary membrane module useable in the apparatus of FIG. 5.
Figure 10A:
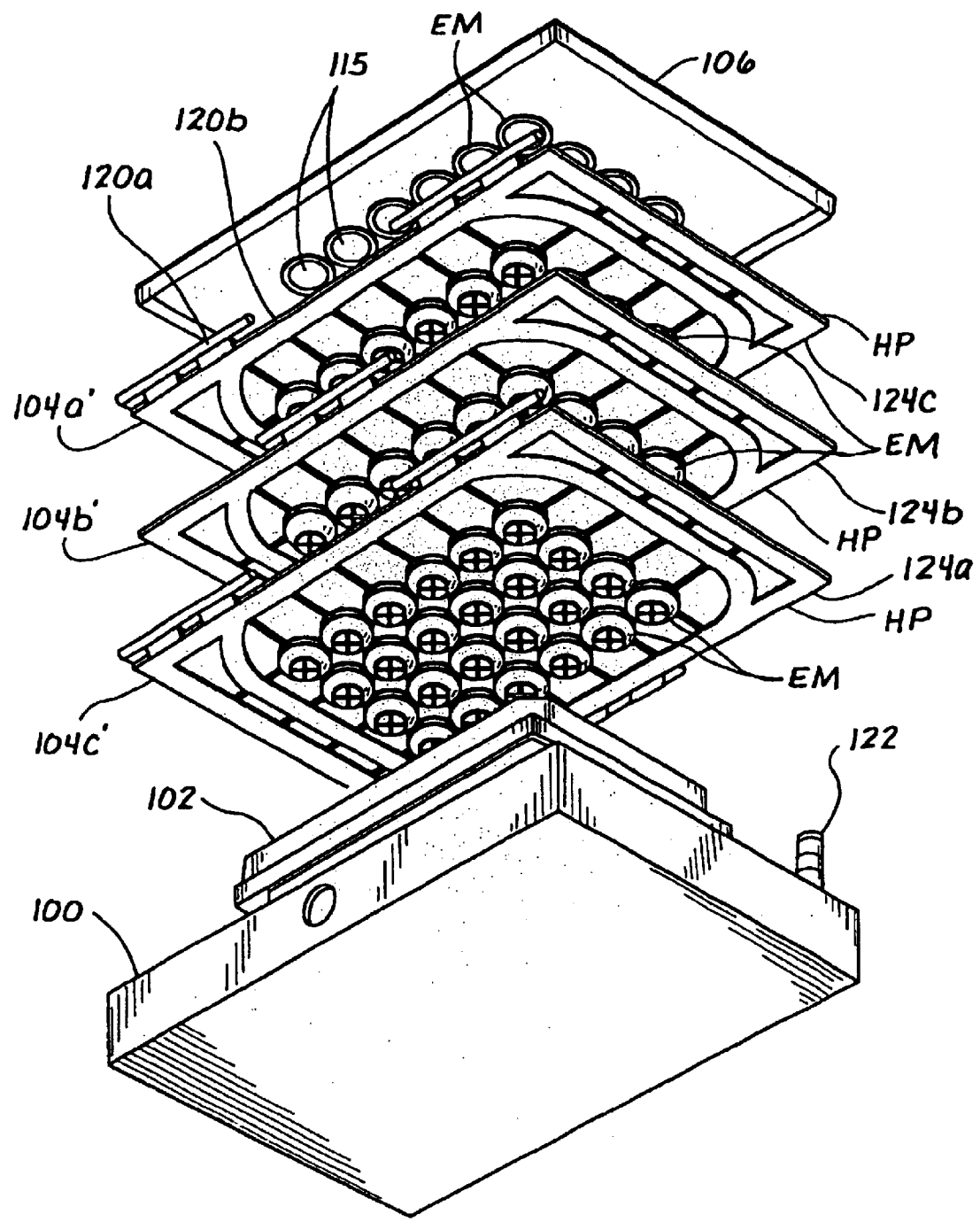
FIG. 10a is a showing of the test apparatus of FIG. 10 from an angle which allows one to visualize the undersides of the component parts of the apparatus, and wherein modified plate-type membrane modules have been incorporated.

FIG. 10a shows another view of the above-described second embodiment of the test apparatus 10a(mod) wherein modified plate-type membrane modules 104a', 104b', 104c' have been incorporated. Each of these modified plate-type membrane modules 104a', 104b', 104c' are formed of two (2) materials—a hard polymer HP and an elastomer EM. Specific examples of the preferred hard polymer HP and elastomer EM are referred to above in relation to the first embodiment (FIGS. 8–9). As shown, an annulus or ring of elastomer EM is formed about the underside of each membrane cavity, so as to abut with the wall of the membrane cavities of the module 104b', 104c' positioned therbelow. In this manner, the elastomer EM serves to form a substantially air tight seal between adjacent membrane modules 104a', 104b', 104c'. Also, elastomer EM pads 119 are formed on the underside of the lid 106, around each air inlet port 115, and such pads 119 abut against the upper surface of the membrane module 104a', 104b', 104c' positioned therebelow to form a discreet, substantially air tight seal therebetween. This effectively isolates each sample flowpath, and prevents escape or leakage of air pressure which could interrupt the desired pressure differential used to propel the sample through the membranes 108a', 108b', 108c'.

Also, optional handles 120a, 120b are formed on the membrane modules 104a', 104b', 104c' to facilitate separation of the modules 104a', 104b', 104c' after the initial filtration has been completed.

Additionally, orientation registry members, such as a post 122 and apertures 124a, 124b, 124c may be formed as shown to prevent the membrane modules 104a', 104b', 104c' from being installed in the incorrect rotational orientation.

iii. Third Embodiment of Test Apparatus

Figure 5A:
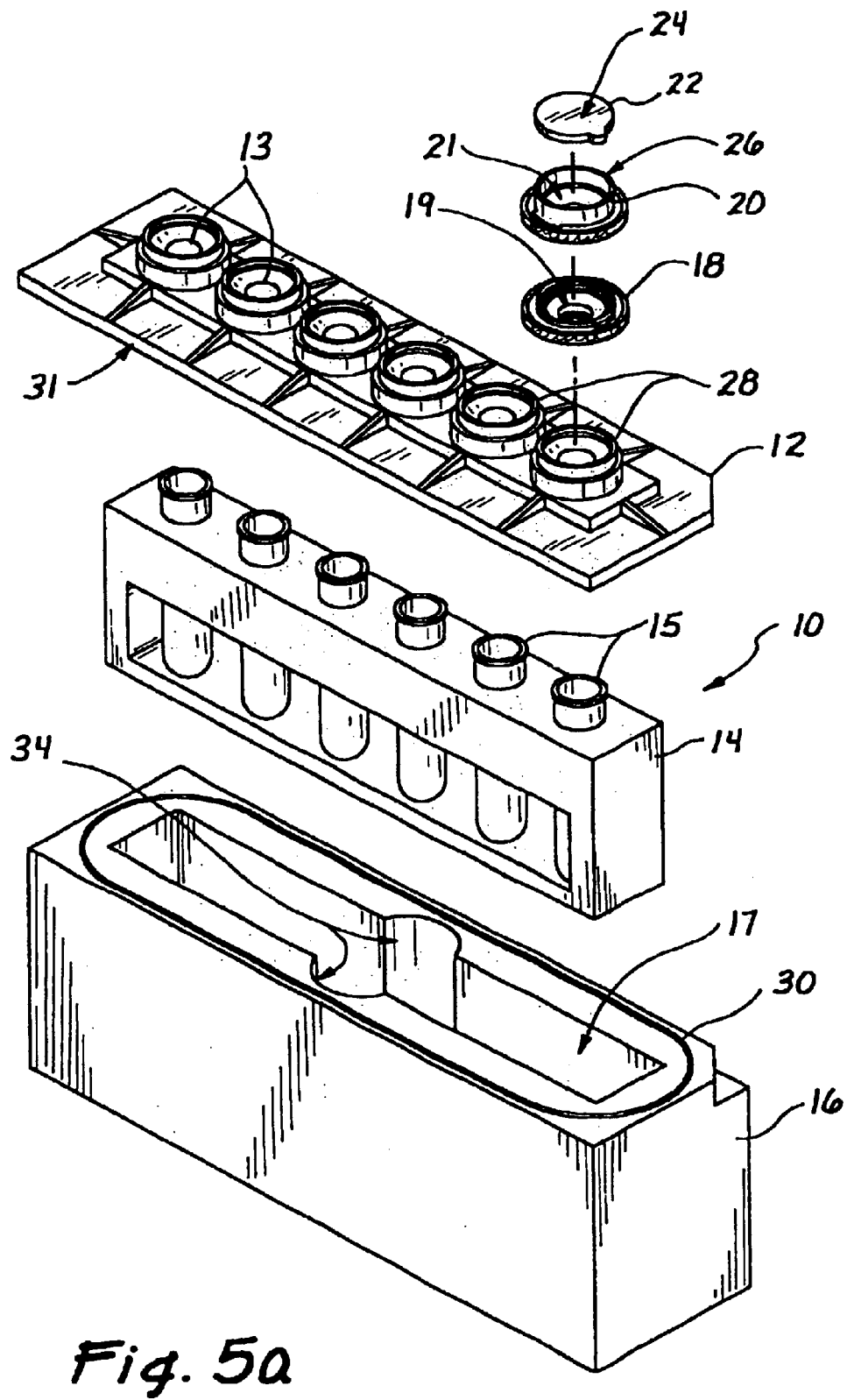
FIG. 5a is an exploded perspective view of the apparatus of FIG. 5.
Figure 6:
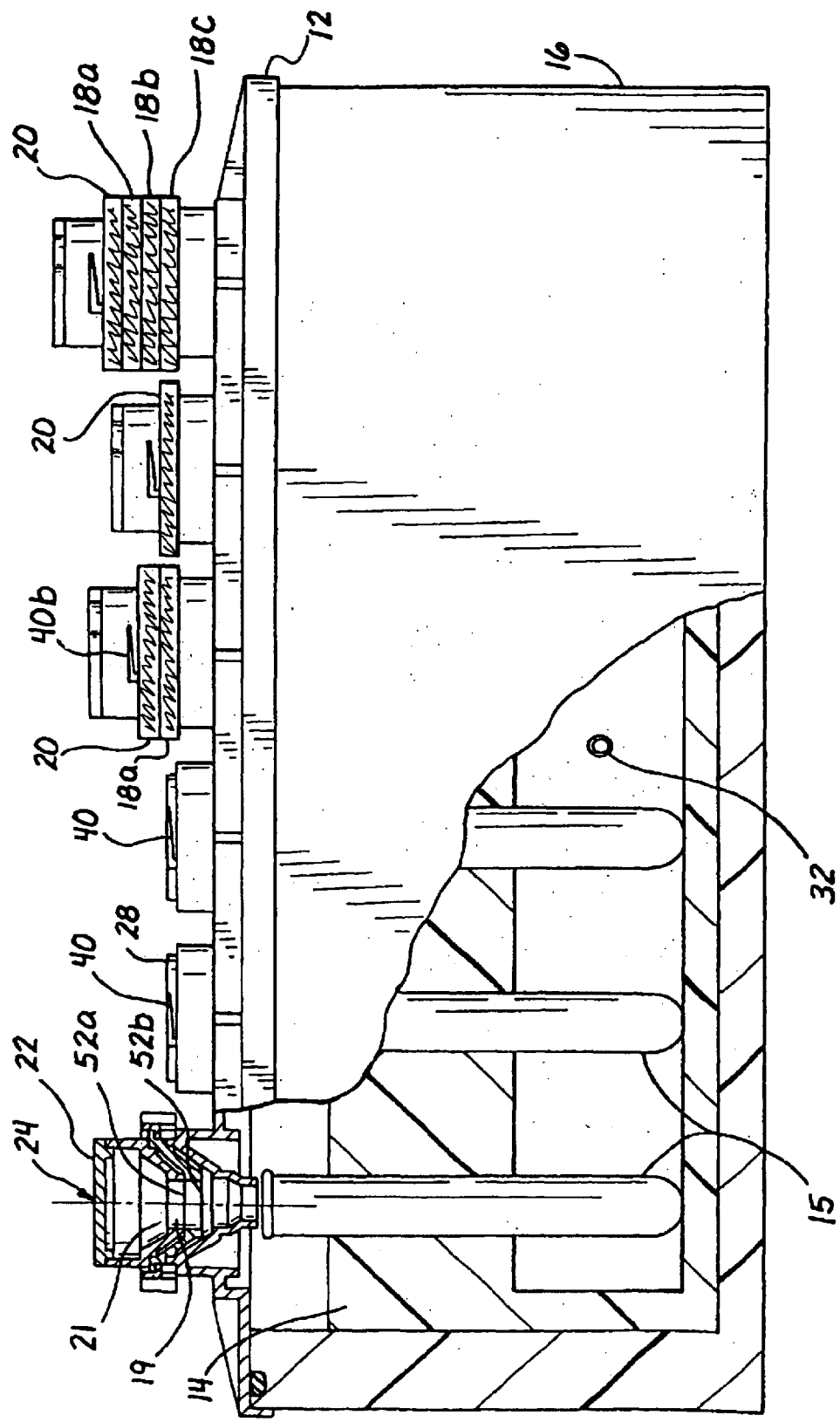
FIG. 6 is a cut-away, side elevational view of the apparatus of FIG. 5, showing the manner in which varying numbers of membranes may be employed in order to determine varying numbers of analytes.
Figure 7:
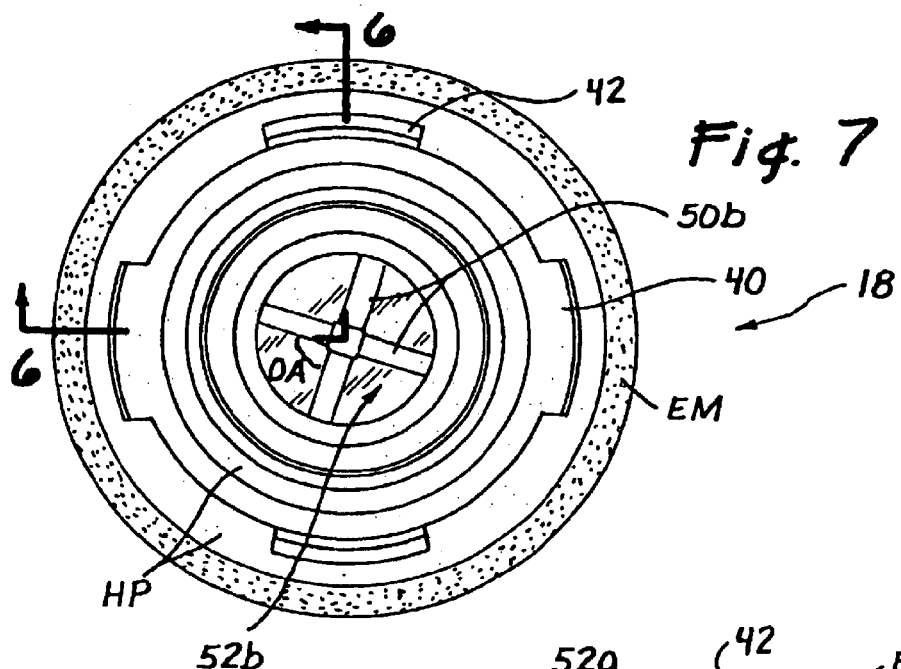
FIG. 7 is top plan view of a secondary membrane module useable in the apparatus of FIG. 5.
Figure 11:
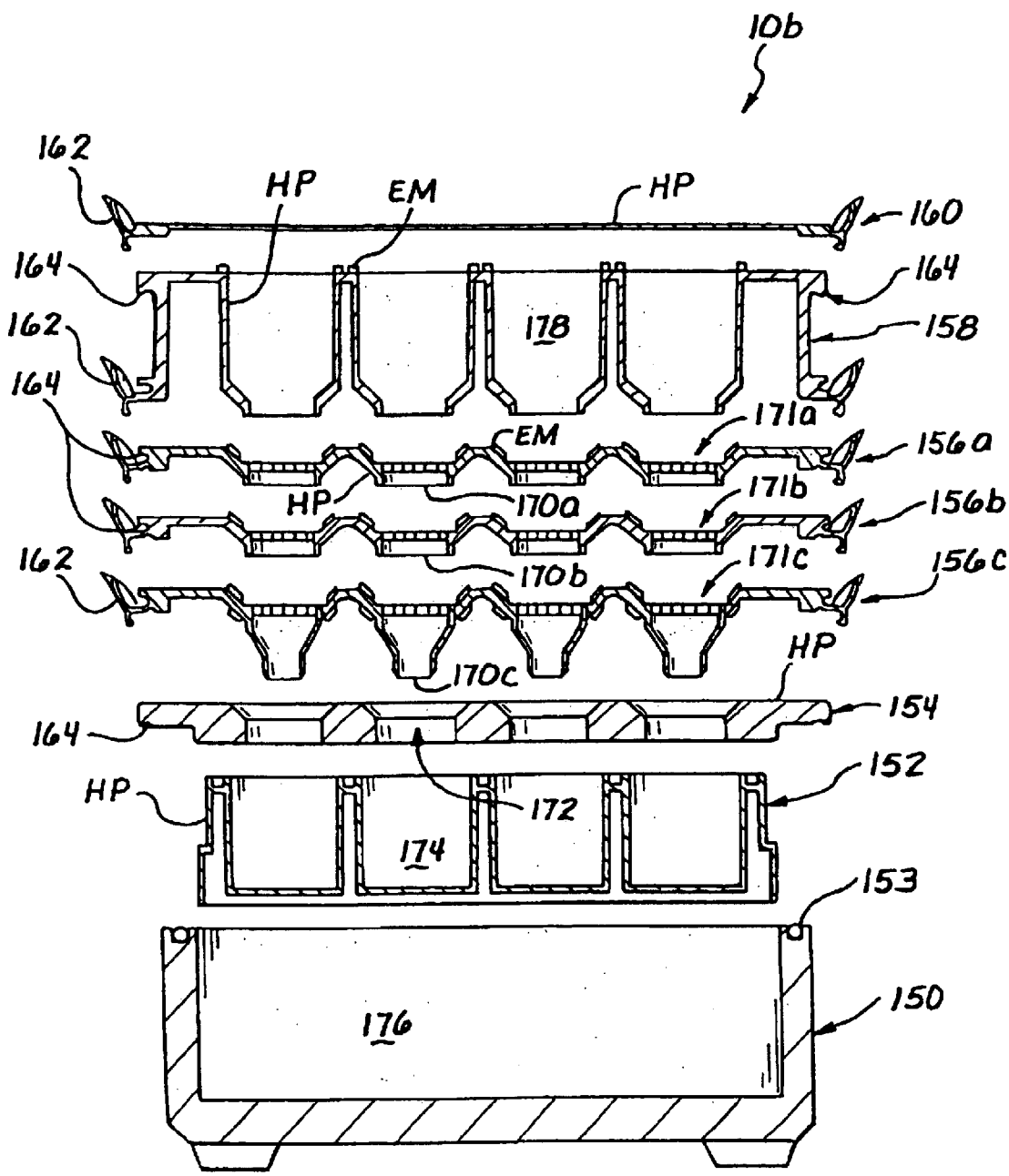
FIG. 11 is a schematic, sectional view of the a third embodiment of a test apparatus of the present invention.

FIG. 11 shows a third embodiment of a test apparatus 10c which comprises a) a vacuum base 150 having a cavity 176 formed therein, b) a receiving unit 152 having a plurality of receiving wells 174 formed therein, c) a support member 154 having a plurality of apertures 172 formed therein, d) plate-type membrane modules 156a, 156b and 156c, each having a plurality of cavities 171a, 171b, 171c with open bottoms and membranes 170a, 170b, 170c disposed transversely over the open bottom of each cavity 171a, 171b, 171c, e) a sample receiving unit 158 having a plurality of sample receiving wells 178 formed therein, and f) a lid 160 which may be placed in sealing contact on top of the sample receiving unit and which may have a plurality of limited air inlet openings (not shown) of the type described above with respect to the first and second embodiments (see item nos. 24 on FIG. 5a and 115 on FIG. 10). These components may be assembled in a stacked array, as shown. Each component is provided with a spring loaded, pivoting, latch member 162 which is configured to engage and latch with a notch 164 in the component positioned immediately therebelow.

In routine operation, the receiving unit 152 is inserted into the cavity 176 of the base 150, and the support member 154 is mounted in the base such that it is in sealing engagement with the o-ring 153 which surrounds the top opening of the base cavity 176 and each aperture 172 is positioned over a receiving well 174. The membrane modules 156a, 156b, 156c are stacked upon the support unit 152 such that each cavity 171a, 171b, 171c and its membrane 170a, 170b, 170c are in alignment over an aperture 172 of the support member 154. The latches 162 of the bottom membrane module 156c are engaged with the notches 164 formed in the support the support member 152, and the latches 162 of the upper membrane modules 156a, 156b are engaged with the notches 164 of the neighboring membrane modules 156b, 156c positioned therebeneath. The sample receiving unit 158 is mounted on the upper-most membrane module 156a such that each sample reservoir 178 is positioned over top of a cavity 171a, and the latches 164 of the sample receiving unit are engaged with the notches 164 on the upper-most membrane module 156a.

Quantities of sample are initially deposited in sample-receiving reservoirs 178 and the lid 160 is mounted in sealing contact on top of the sample receiving unit 158 with the latches of the lid 160 in engagement with with the notches 164 of the sample receiving unit 158. Thereafter, a source of negative pressure is connected to a port (not shown) formed in the base 150 so as to create negative pressure within the cavity 113 of the base 150. This negative pressure causes each sample to be drawn downwardly through the membranes 170a, 170b and 170c positioned under that sample reservoir 178, and the resultant filtrate to be received in the particular receiving well 174 positioned under those particular membranes. In this manner, this third embodiment of the test apparatus 10b may be used to simultaneously process a plurality (e.g., 24 or 48 separate samples).

Typically, the membranes 171a of the first membrane module 156a are for the purpose of filtering out or removing interferants, particles or other unwanted matter while the membranes of any secondary membrane modules 170b, 170c are for capturing analytes for subsequent concentration and/or analysis. Accordingly, after the initial filtrate has been received in the filtrate receiving wells 174, the vacuum source is terminated or disconnected, differential pressure within the apparatus 10a is allowed to equalize to a point where removal of the lid 115 will not cause substantial upward bulging or rupture of the membranes 170a, 170b, 170c, and the lid 160 is unlatched and removed. All of the membrane modules 156a, 156b, 156c are then removed and the first membrane module 156a (along with the particles, interferants and/or other unwanted matter removed by its membranes 170a) is discarded.

Thereafter, the receiving unit 152 is removed and appropriate reagent(s) are added to the filtrate contained within the receiving wells 174 to provide a filtrate-reagent admixture from which a desired first analyte (Analyte A) may be qualitatively or quantitatively determined.

In applications such as that shown in FIG. 11, where secondary plate-type membrane modules 156b and/or 156c are used, such secondary membrane modules 156b, 156c will typically have captured secondary analyte(s) (Analytes B, C, etc.) which are to be subsequently released from the membranes 170b, 170c and thereafter concentrated and/or determined. In furtherance of this, a clean receiving unit 152 may be inserted into the cavity 176 of the base 150, and one of the secondary membrane modules 156b or 156c is then positioned on top of the new receiving unit 152 such that each membrane 170b or 170c is positioned over a receiving well 174. A known volume of flush solution or eluant is then placed in the cavity 171b or 171c above each membrane 170b or 170c, and the lid 160 is replaced such that it is latched to the notches in the membrane module in use 156b or 156c and in sealing contact with the support member 154. The vacuum source is then re-energized or reconnected to the base 150 to cause a differential pressure to be once again established within the apparatus 10b. In this manner the flush solution or eluant is drawn downwardly through the membranes 170b or 170c so as to extract or release the captured analyte(s) from the membranes 170b or 170c. An eluant/analyte mixture is thus received within each receiving well 174, and the above described procedure is repeated to qualitatively or quantitatively determine that analyte in the eluant/analyte mixture within each receiving well 174.

The same procedure is then repeated for each additional secondary membrane module 156b, 156c, until all analytes have been determined.

iv. Fourth Embodiment of Test Apparatus

FIGS. 12 and 12a show a top-pressurized fourth embodiment of a test apparatus 10c of the present invention. This fourth embodiment utilizes positive pressure applied to the top of the apparatus 10c rather than negative pressure applied to the bottom of the apparatus as in the above-set-forth first, second and third embodiments.

This apparatus 10c generally comprises a) a base 190, b) a receiving unit 192 having a plurality of receiving wells (not shown) formed therein, c) a support hood 194 having a plurality of apertures 196 formed therein, d) first and second membrane modules 198a, 198b, and e) a positive pressure lid 200.

Each membrane module 198a, 198b has a plurality of individual sample passage channels 210 formed therein. A membrane 216 is disposed transversely within each sample passage channel 210. Membrane support cross-members 214, such as those described hereabove with respect to the first embodiment (see item nos. 50a, 50b and 41 of FIGS. 7–9) may optionally be formed within the sample passage channels 210 to support and deter tearing or rupture of the membranes 216.

The operation of this test apparatus 10c is generally consistent with that described hereabove in reference to the first, second and third embodiments 10, 10a, 10b, except that rather than drawing the sample through the membranes 210 by way of negative pressure applied beneath the membranes, this apparatus 10c pushes the sample through the membranes 210 by way of positive pressure applied to the positive pressure lid 200.

Modified Membrane Module for Fourth Embodiment

Figure 13:
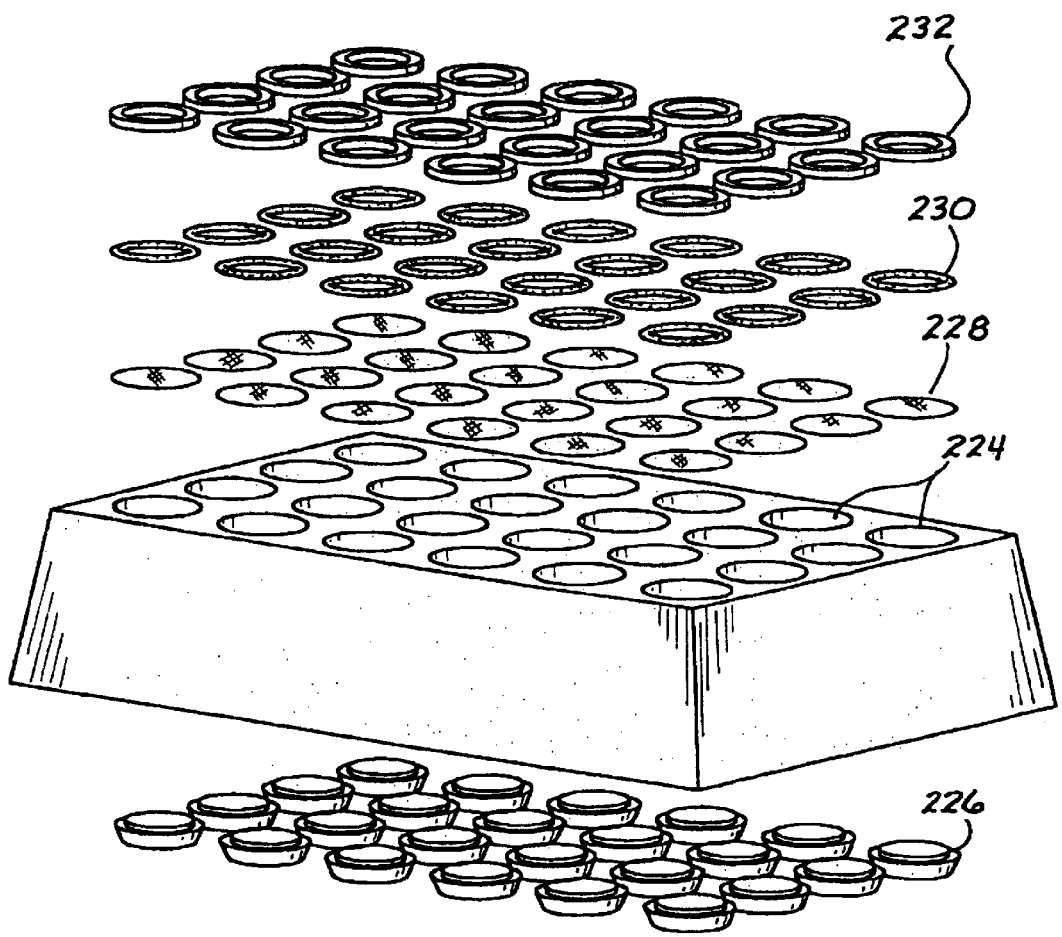
FIG. 13 is an exploded view of an alternative membrane module useable in the apparatus of FIG. 12.

FIGS. 13 and 13a shows a modified "top loaded" membrane module 198a' which comprises a housing 220 having a plurality of cylindrical bosses formed downwardly therein such that the wall 221 of each cylindrical boss defines a sample passage channel 224. Each channel 224 has a membrane support floor 240 formed transversely therein. A filtrate-flow opening 242 is formed through each membrane support floor 240, and a plurality of raised membrane mounting surfaces 244 are formed on the upper surface of each membrane support floor 240. Disc shaped membranes 228 are placed flat upon the membrane mounting surfaces 224, and o-rings or seals 230 are then passed downwardly into each channel 224 and are disposed in contact with the wall of the channel 224, on top of and in contact with the periphery of each membrane 228. Sealing ring members 232 are then inserted downwardly into each channel 224 and are affixed to the wall of the channel 224 to compress the o-rings or seals 230 and to thereby hold the membranes 228 in captured, fixed position between the o-rings or seals 230 and the underlying membrane support floor 240. The areas between the raised membrane mounting surfaces 244 provide spaces through which filtrate which passes downwardly through each membrane 228 may drain through filtrate flow openings 242.

Figure 14A:
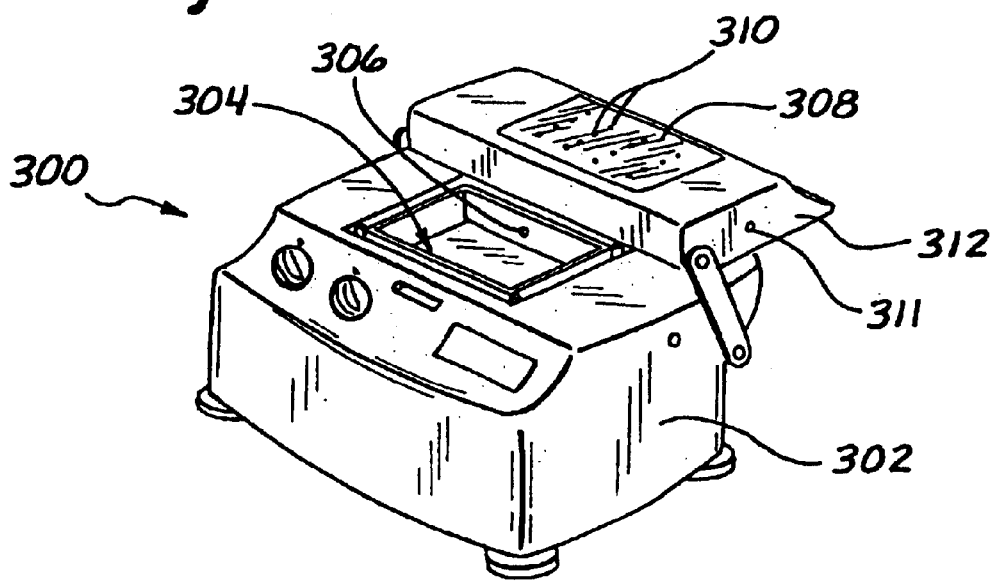
FIG. 14a is a perspective view of a vacuum base apparatus useable with some of the test apparatus of the present invention, wherein the top cover of the vacuum base apparatus is in an open position.
Figure 14B:
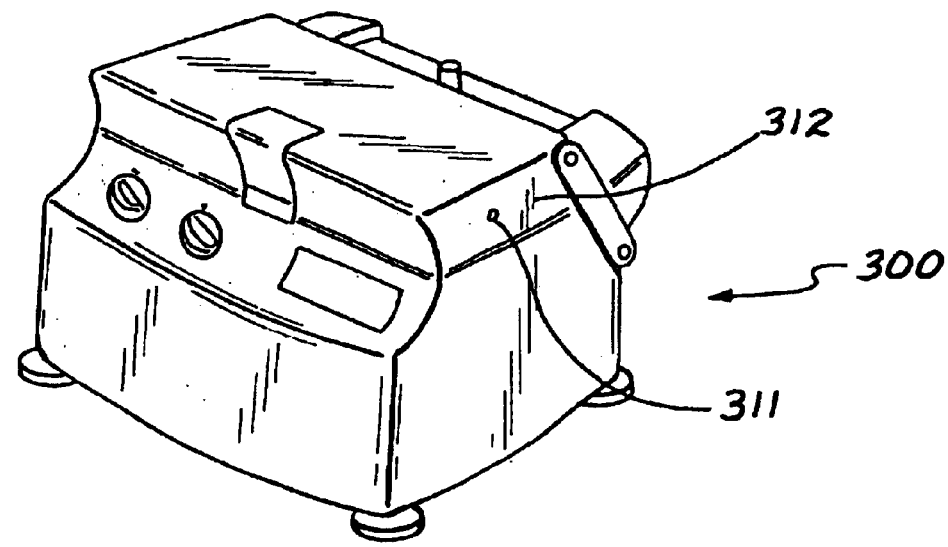
FIG. 14b is a perspective view of a vacuum base apparatus of FIG. 14a, with its top cover in a closed position.

Elastomeric sealing rings 226 (e.g., o-rings) are then passed around the outer surface of the wall 221 of each cylindrical boss to form a seal between that membrane module 198a and the neighboring membrane module or support unit 154 positioned therebelow.

v. A Negative Pressure Base Unit Adaptable for use with Various Embodiments of Test Apparatus FIGS. 14a and 14b show a self contained negative pressure base unit 300 which is adaptable to replace the negative pressure base units of certain embodiments of the test apparatus, such as base units 16 (FIG. 5) and 100 (FIG. 10). This self-contained negative pressure base unit 300 incorporates an internal vacuum pump (not shown) so as to eliminate the need for use of a separate vacuum source.

This self-contained negative pressure base unit 300 comprises a housing 302 having a cavity 304 formed therein and a lid 312 which, when closed, forms a substantially air tight seal of the cavity 304. An elastomeric pad 308 is formed on the underside of the lid 312. Such elastomeric pad 308 abuts and seals against the component of the test apparatus (e.g., the upper membrane module 104a, 104a' or 156a). A plurality of limited air inlet openings 310 are formed at locations in the lid 312 to operate in the same manner and perform the same function as the air inlet openings 24, 115 of the first and second embodiments described above. A make up air manifold (not shown) connects each air inlet opening 310 to a single make-up air port 311 formed in the side of the lid 312.

In operation, the filtrate receiving and membrane module components of the test apparatus are inserted into the cavity 304, the lid 312 is closed, and the internal vacuum pump (not shown) of the base apparatus 300, is used to draw the sample through the membrane(s) as described repeatedly hereabove. When all samples have been drawn through the respective membranes, the vacuum pump (not shown) is de-energized, the pressure differential within the apparatus is allowed to equalize, and the lid 312 is opened to allow the operator to remove the test apparatus and proceed with determination of the analyte(s) in accordance with the invention.

vi. A Fifth Embodiment of Test Apparatus

FIGS. 15a–15e show yet another (i.e., fifth) embodiment of the test apparatus of the present invention, which is useable in conjunction with the membrane modules 18, 20 and lids 22 of the above-described first embodiment 10. (see FIGS. 5–9). This test apparatus 10d is constructed for simultaneous analysis of multiple (e.g., six (6)) samples, and comprises a base unit 500 having a plurality of test tube receiving cavities 502 formed therein. A lid 504 is mountable in sealing contact on the base 500, and such lid 504 incorporates a plurality of sample ports 506 having sample passage channels 508 extending downwardly therethrough. As shown, the primary and secondary membrane modules 18, 20a, 20b (FIGS. 7–9) are engageable with the sample ports 506 of this apparatus, in the same manner and to perform the same function as described above with reference to the first embodiment of the test apparatus 10. A vacuum source is connectable to the base 500 to draw the desired vacuum within the cavity Alternative Self-Contained Vacuum Base Unit for Fifth Embodiment The base 500 of the fifth embodiment 10d, may be replaced by a self-contained base unit 510 of the type shown in FIG. 15e. This self-contained vacuum base unit 510 has a plurality of test tube receiving cavities 502' formed therein, as shown. After clean test tubes have been inserted into the cavities 502', the above-described lid 504, membrane modules 18, 20a, 20b and lids 22 are applied and utilized in the manner fully described elsewhere in this application.

vii. A Self-Contained Combination Base Unit

FIG. 16 shows a self-contained combination base unit 510a which is useable with several different embodiments of the test apparatus, such as the second 10a and fifth 10d embodiments described above. This combination base unit 510a comprises a housing 511 having a cavity 304' and all of the same elements as the self contained negative pressure base unit 300 shown in FIGS. 14a and 14b, but additionally including a vacuum station 512 which is designed to provide negative pressure to the test apparatus 500 shown in FIGS. 15a–15e. In this manner, a vacuum connection nipple 514 is formed in the vacuum station, and is insertable into a corresponding vacuum connection fitting (not shown) on the base 500 of the test apparatus 10d. Shoulders 516 are configured to hold the test apparatus 10d on the vacuum station 516, when in use. An internal check valve or cap is used to close off the vacuum connection nipple 514 when the test apparatus 10d is not mounted theron.

viii. A Dip Stick Test Apparatus

FIG. 17 shows a sixth embodiment of the test apparatus of the present invention. This sixth embodiment comprises a dipstick 700 having a handle 702, a first (i.e., outer) membrane 704 and a second (i.e., inner) membrane 706. The second membrane 706 is substantially surrounded and enclosed by the first membrane 704 such that only filtrate which has passed through the first membrane 704 will come into contact with the second membrane 706. The first (i.e., outer) membrane is typically a micro-porous membrane which serves to prevent particles or large molecules which exceed a certain molecular weight from passing therethrough. Examples of molecular weight cut-off membranes which may be useable as the first membrane 704 include the Sartorious™ 1000 MW cut off, 3000 MW cut off, or 5000 MW cut-off, as specified in Table III. The second (i.e., inner) membrane is typically an indicator membrane which is impregnated with or which bears an indicator substance, such as a dye, which will undergo some perceptible change (e.g., a color change) when contacted by a certain analyte or a predetermined concentration of a certain analyte. The second membrane 706 may be adapted for a) qualitative determination of a particular analyte (e.g., the second membrane 56 undergoes a single color change occurs in the presence of a certain analyte irrespective of the concentration in which that analyte is present; b) semi-qualitative determination of a certain analyte (e.g., the second membrane undergoes a single color change only if contacted by a certain analyte which is present at or above a predetermined threshold concentration, or c) quantitative determination of the concentration of a particular analyte (e.g., the second membrane 56 undergoes a scaled color change such that the shade or color of the second membrane is indicative of the concentration at which the analyte is present.

In operation, the user grasps the handle 702 of the dipstick apparatus 700 and dips the end of the dipstick apparatus 700 opposite its handle 702, into a liquid or gaseous matrix (e.g., a solubilized food product, an oil, a biological fluid, etc.) Such that the first (i.e., outer) membrane 704 is fully or partially immersed in the matrix. A filtrate of the matrix then permeates the first (e.g., outer) membrane 704 and comes into contact with the second (i.e., inner) membrane 706. The second (i.e., inner) membrane then undergoes an indicative change (e.g., a color change) which correlates to the presence of the target analyte (or the predetermined concentration of the analyte).

C. Specific Test Kits & Methods

TABLE I sets forth a number of test kits/assay methods of the present invention, and provides specific information as to the analyte(s), membrane(s), reagent(s) and detection method(s) used in each such test kit/assay method. In TABLE I, each horizontal row sets forth a particular test kit/method of the present invention. The columns of each horizontal row are, from left to right, as follows:

First Column: the first column indicates the analyte(s) which are determined;

Second Column: the second column indicates the typical matrices in which the analyte(s) are contained;

Third Column: the third major column labeled "membranes" indicates the type of (i) first membrane ($M_1$), (ii) second membrane ($M_2$), (iii) third membrane ($M_3$), and (iv) fourth membrane ($M_4$);

Fourth Column: the fourth major column labeled "reagents" indicates the (i) first reagent ($R_1$) to be combined with the first filtrate in the first vessel for detection of the first analyte, (ii) second reagent ($R_2$) to be combined with eluant from the second membrane (if any) in a second vessel for detection of the second analyte (if any), (iii) third reagent ($R_3$) to be combined with eluant from the third membrane (if any) in a third vessel for detection of the third analyte (if any), and (iv) forth reagent ($R_4$) to be combined with eluant from the fourth membrane (if any) in a fourth vessel for detection of the fourth analyte (if any);

Fifth Column: the fifth column indicates the preferred analytical method or instrument used to determine each analyte; and Sixth Column: the sixth column sets forth other information which is particular to that test kit/method.

The TABLE II is a key to the acronyms used to designate the various analytes, membranes, reagents and detection methods in TABLE I.

TABLE III provides a list of commercially available membranes which correspond to the acronyms used to refer to the membranes in TABLE I. TABLE IV is a table listing algorithms which are useable in conjunction with certain test kit & methods of the present invention to predict or discern certain factors such as shelf life, presence of contaminants, potential for oxidative degradation, etc., as described more particularly herebelow with respect to certain assays which are of predictive value.

EXAMPLES OF TEST KITS/METHODS FOR QUALITATIVE AND/OR QUANTITATIVE DETERMINATION OF SELECTED ANALYTES

The following are detailed examples of the use of specific test kits/methods of the present invention, which may be performed using the test apparatus of the present invention. The term "protectants" as used in the following examples means compound(s) capable of inhibiting or preventing the occurrence of certain changes in the analyte(s), such as one or more antioxidants (e.g., ascorbic acid 1%, BHT 0.1%, or tocopherols 0.01–1.0%) capable of deterring oxidation and/or compounds capable of chelating or binding metals (e.g., EDTA <0.1%). The term "stabilizers" as used in the following examples means one or more substances capable of preventing denaturation of a proteinaceous analyte (e.g. albumen 0.1–10.0%) or conformational/structural changes of any analyte. The term "solubilizers" as used herein means one or more surfactants or other substances capable of promoting dissolution of an analyte (e.g., Tween 80, Tween 20, sodium dodecyl sulfate (SDS), benzyl (BAC), etc.)

Example 1

Free Fatty Acids in Oils or Oil Components

A test kit/method for determining the amount of free fatty acids in oils and oil components either qualitatively or quantitatively. The oils or oil components may be present in a matrix such as a food, personal care product, cosmetic or other complex matrix. This example is performed in accordance with row 1 of the TABLE I.

A. A sample of the matrix is initially diluted with a diluent such as isopropanol with or without protectants. The sample may, or may not be, processed through a membrane to remove particles, proteins or other interferants, depending on whether such matter is present in the matrix. For clean oils, such membrane processing may be unnecessary.

B. A dye which is sensitive to concentration of free fatty acid for its spectral properties (e.g., Xylenol Orange) is solubilized in a diluent such as isopropanol with or without protectants.

C. A control or standard is prepared by dissolving known concentrations (e.g., 0.00% to 5.00%) of the analyte (e.g.free fatty acids) in a diluent such as isopropanol.

D. The solutions prepared in steps A and B or C and B above, are combined and read spectrophotometrically at the peak most sensitive to acidity of the dye and results of samples are compared to results obtained from the standards.

E. For Xylenol Orange between 0.001% to 10.0% in isopropanol this peak is between 540 and 600 nM with the optimal choice at 570 nm. A decrease in the absorption at this peak increases with acidity on a logarithmic basis and this is used to determine the free fatty acid for the oil (i.e. a log-logit curve plot).

F. This can be done utilizing any spectral device measuring absorption at the wavelength for that dye.

G. Sample blanks can be run if necessary for very colored substances, as can blanks for standards.

Example 2

Free Fatty Acids in Oils and Other Matrices

A test kit/method for determining the amount of free fatty acids in oils and oil components in food, personal care, cosmetics and other matrices which contains the following reagents for analyzing liquids undiluted or diluted in reagents based in solvents, solvent mixtures, or water or water/solvent mixtures. This example is performed in accordance with Row 1 of TABLE I.

A. The oil or oil containing extract is dissolved or disbursed in a diluent (e.g., methanol, isopropanol, hexane or combinations thereof) with or without protectants, and may be processed through a membrane if needed, in accordance with row 1 of TABLE I.

B. A dye sensitive to concentration of acid for its spectral properties (e.g. Xylenol Orange) is solubilized in a diluent e.g., methanol, isopropanol, hexane or combinations thereof) with protectants as necessary.

C. A control or standard prepared from free fatty acids or prepared oil and standard compounds in isopropanol or any solvents listed above at specified level of free fatty acids of 0.00% to 5.00% free fatty acids.

D. Where A and B or C and B are combined and read at the peak most sensitive to acidity of the dye and results of samples are compared to results obtained from the standards.

E. For Xylenol Orange between 0.001% to 10.0% in isopropanol or any of the solvents listed above including water or water/isoporpanol mixtures or water/solvent mixtures this peak is between 540 and 600 nm with the optimal choice at 570 nm. A decrease in the absorption at this peak increases with acidity on a logarithmic basis and this is used to determine the free fatty acid for the oil (i.e. a log-logit curve plot). This can be done utilizing any spectral device measuring absorption at the particular wavelength.

F. Sample blanks can be run if necessary for very colored substances as can blanks for standards.

Example 3

Free Fatty Acids in Oils and Oil Components in the Presence of Particles, Proteins, and/or Other Interferants A test kit/method for determining the amount of free fatty acids in oils and oil components in food, personal care, cosmetics and other matrices. The test kit contains the following reagents for analyzing liquids undiluted or diluted, and utilizes a single or stacked membrane preparation of the matrix to remove particles, protein, or other interferants (e.g., metals). This example is performed in accordance with row 1 of TABLE I.

A. A sample of the matrix is dissolved or mixed (e.g., by vortexing) in a diluent (e.g., methanol, isopropanol, hexane or combinations thereof) with or without protectants.

B. The diluted sample is passed through a first membrane such as an MCE membrane to remove particulate matter.

C. The filtrate which passes through the first membrane is then passed through a second membrane such as a metal capturing membrane (e.g., an imino-diacetic acid membrane (IDA) as referred to in TABLE IV), if necessary, to remove additional compounds which would bind with the substrate sensitive to acidity or to bind inorganic acids as to contribute background acidity levels.

D. A dye sensitive to concentration of acid for its spectral properties (e.g., Xylenol Orange) is solubilized in isopropanol with protectants, as necessary.

E. A control and/or standards containing known concentrations of free fatty acids (e.g., 0.00% to 5.00%) may be prepared from free fatty acids or prepared oil and standard compounds in isopropanol.

F. The solutions obtained in steps (C and D) and (E and D) are combined, and are read spectrophotometrically at the peak most sensitive to acidity of the dye, and results of samples are compared to results obtained from the standards.

G. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid for the oil. (e.g., a log-logit curve plot). This can be done utilizing any spectral device measuring absorption at the particular wavelength H. Sample blanks can be run if necessary for very colored substances as can blanks for standards.

Example 4

Dip Stick Test for Free Fatty Acids in Oils and Other Matrices

A dip stick test kit/method for determining the amount of free fatty acids in oils and oil components in food, personal care, cosmetics and other matrices. The test kit contains the following reagents for analyzing liquids, undiluted or diluted.

A. A sample of the matrix is dissolved or mixed in a preparation reagent such as isopropanol with or without protectants.

B. A dye sensitive to concentration of acid for its spectral properties (e.g., Xylenol Orange or Thymol Blue) or other dye(s) which undergo color changes in the range of pH 6 to pH 8 is/are attached to a membrane of a dip stick (e.g., the inner membrane if an outer filtering membrane is present on the dip stick) of the type shown in FIG. 17.

C. A control and/or standards containing known concentrations of free fatty acids (e.g., 0.00% to 5.00%) may be prepared from free fatty acids or prepared oil and standard compounds, in isopropanol.

D. The dip sticks are dipped in the solutions obtained in steps A and C, and the color of the dye in the dip stick dipped into each sample is compared to the color of the dye of the dipsticks dipped into the standard solutions, to obtain a semi-qualitative determination of the concentration of free fatty acids in the samples.

Example 5

A One Vial Test for Free Fatty Acid in Oils and Oil Components

A semi-quantitative, one-vial test kit/method for determining the amount of free fatty acids in oils and oil components in food, personal care, cosmetics and other matrices. The test kit contains the following reagents for analyzing liquids, undiluted or diluted. This example is carried out in accordance with row 1 TABLE I.

A. A sample of the matrix (e.g., a sample from a bottle of salad oil at home or in a restaurant, a sample of oil obtained during manufacture/bottling) is dissolved or mixed in isopropanol with or without protectants, and may or may not be processed through a filtering membrane depending on whether particles or other interferants are believed to be present.

B. A dye sensitive to concentration of acid for its spectral properties, such as Xylenol Orange, solubilized in isopropanol with protectants, as necessary, is provided in pre-filled vials.

C. A control and/or standards containing known concentrations of free fatty acids (e.g., 0.00% to 5.00%) may be prepared from free fatty acids or prepared oil and standard compounds in isopropanol.

D. The solutions obtained from steps (A and B) and (C and B) are combined, and equal amounts of each such mixture are dispensed into the dye-containing vials. The resultant color change in each vial is read visually and results of samples are compared to results obtained from the standards, if necessary, or to a visual chart or color wheel.

E. For Xylenol Orange between 0.001% to 10.0% in isopropanol this color is first blue but changes to yellow in the presence of at least a predetermined concentration (e.g. 3.0%) of free fatty acid. Thus, this test kit with such concentrations of Xylenol Orange can be used to determine whether a certain sample of olive oil may be labeled as "extra virgin" (i.e., contains less than 3.0% free fatty acids) or whether a sample of used cooking oil should be deemed no longer usable (i.e., contains more than 3.0% free fatty acids).

F. An adjustment in the Xylenol Orange concentration can be made to allow the test kit to be used to determine any free fatty acid concentration between 1.0% and 3.0%.

Example 6

Free Fatty Acid in Olives or Olive Oils

A test kit for determining whether a sample of olive oil qualifies as "extra virgin", "virgin" or "virgin corrente" based on the concentration of free fatty acids present therein, or for determining whether aged oils are acceptable for human consumption, or for pre-testing of olives to select those olives which will provide the highest quality oil. The test kit contains the reagents and membranes (if membranes are needed) as specified herebelow. This example is in accordance with row 1 of TABLE I.

A. A sample of the oil or oil containing extracts is dissolved or mixed in a preparation reagent such as isopropanol, with or without protectants, and may be processed through a filtering membrane if so required. For clean oils, such membrane may be unnecessary.

B. A dye sensitive to concentration of acid for its spectral properties, such as Xylenol Orange, solubilized in isopropanol with protectants, as necessary.

C. A control and/or standards containing known concentrations of free fatty acids (e.g., 0.00% to 5.00%) may be prepared from free fatty acids or prepared oil and standard compounds in isopropanol.

D. The solutions obtained from steps (A and B) and (C and B) are combined, and equal amounts of each such mixture are dispensed into the dye-containing vials. The resultant color change in each vial is read visually and results of samples are compared to results obtained from the standards, to determine free fatty acid concentration.

E. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid for the oil (i.e. a log-logit curve plot). This can be done utilizing any spectral device measuring absorption at the particular wavelength F. Sample blanks can be run if necessary for very colored substances as can blanks for standards.

G. The free fatty acid concentrations determined by this test are then used to catagorize the olive oil or oil containing olive extract, in one of the following categorys:

| | |
|---|---|
| 0 to 1% FFA | extra virgin |
| 1 to 2% | virgin |
| 2 to 3% | virgin corriente (syn. "virgin common") |
| more than 3% | not for human consumption |

Example 7

Free Fatty Acid and Polyphenols in Olive Oils or Olives to Determine Oil Quality and Long Term Stability A test kit for qualitatively determining the amount of free fatty acids in oils and oil components in foods in combination with a polyphenol test which together determines a) oil quality (e.g., extra virgin, virgin, virgin corriente as described in Example #6 above and b) long term stability based on polyphenol content (the higher the polyphenol concentration the longer the stability). This example is in accordance with row 11 of TABLE I.

A. A sample of the oil or oil containing extracts is dissolved or mixed in a preparation reagent such as isopropanol, with or without protectants and processed through the membranes shown on row 11 of TABLE I.

B. A dye sensitive to concentration of acid for its spectral properties, such as Xylenol Orange, solubilized in isopropanol, with protectants as necessary, is provided for free fatty acid determination.

C. A dye sensitive to phenol such as folin ciocalteau reagent in water/isopropanol with sodium carbonate, is provided to determine the polyphenol concentration.

D. A control and/or standards containing known concentrations of free fatty acids (e.g., 0.00% to 5.00%) and polyphenols (e.g., 2 to 200 micrograms/gram) may be prepared from free fatty acids or prepared oil and standard compounds in isopropanol.

E. The solutions obtained from steps A and D above are dispensed into vials containing the Xylenol Orange and folin ciocalteau reagents. The resultant colored sample solutions are read visually or spectrally, and the samples are compared to the standard solutions to determine free fatty acid and polyphenol concentrations.

F. A Xylenol Orange/isopropanol solution having a dye concentration between 0.001% and 10.0% will initially be of a blue color, but will change to yellow in the presence of more than about 1% free fatty acid. Such discernment of free fatty acid concentrations in excess of 1% allows the operator to immediately determine whether an olive oil should be labeled as "not extra virgin" or a cooking oil should be labeled as "no longer usable". If it is desired to diferentiate between higher concentrations of free fatty acids (e.g., 2% or 3%) the Xylenol Orange concentration may be increased so that the solution will change to a yellow color at the higher concentration (e.g., 2% or 3%) of free fatty acids.

G. Generally, in this example, a deep blue color of the sample solution indicates good stability with substantial amounts of polyphenol and antioxidant present, whereas a clear solution is very unstable.

H. Polyphenols from 2 to 200 micrograms per gram are determined

I. The free fatty acid values which can be obtained for olive oil either extra virgin, virgin, or virgin common are shown in #6. Polyphenol concentrations in excess of 100 micrograms/gram indicate excellent shelf life, 50 to 100 micrograms/gram indicates very good shelf life, 20 to 50 micrograms/gram indicates good shelf life, and less then 20 micrograms/gram indicates poor shelf life.

Example 8

Lipid Peroxides and Free Fatty Acids in Oils and Oil Components

A test kit for determining the amount of lipid peroxides and free fatty acids in oils and oil components either qualitatively or quantitatively in food, personal care, cosmetics and other matrices which contains the following reagents for analyzing liquids undiluted or diluted. This example may be performed in accordance with either row 2 or row 3 of TABLE I.

A. A sample of the oil or oil containing extracts is dissolved or mixed in a preparation reagent such as isopropanol, with or without protectants. This sample may be processed through membranes in accordance with rows 2 or 3 of TABLE I.

B. A first dye sensitive to concentration of acid for its spectral properties, such as Xylenol Orange, solubilized in isopropanol, with protectants as necessary, is provided for determination of free fatty acids. A second dye, such as Xylenol Orange or non-oxidized hemoglobin in the presence of certain prooxidants such as acidified iron, is provided for determination of lipid peroxides. The preferred embodiment utilizes 0.1% Xylenol Orange and ferrous sulfate (5–200 mM and preferably about 25 mM) in combination with sulfuric acid at 50 to 500 mM (optimum at 140 ml) for determination of lipid peroxides. For determination of free fatty acids, 2.25 ml of the 0.1%Xylenol Orange solution from step B is added to 42.5 ml of isopropanol with 0.1% BHT, to form the fatty acid reagent.

C. A control or standard prepared from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

D. The solutions from steps (A and B) and (C and B) are combined and read spectrally at the peak most sensitive to acidity of the dye, and the results of such readins are compared to results obtained from the standards and the peroxide reaction is read at that peak for the electron recipient at 570 nm.

F. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid (e.g., by a log-logit curve plot). For lipid peroxides the absorption of Xylenol Orange-Fe Complex increases at 570 nm as it receives electrons. This absorption can be read utilizing any spectral device measuring absorption at the particular wavelength G. Sample blanks can be run if necessary for very colored substances as can blanks for standards.

Example 9

Lipid Peroxides and Free Fatty Acids in Oils and Oil Components

A test kit for determining the amount of lipid peroxides and free fatty acids in oils and oil components either qualitatively or quantitatively in food, personal care, cosmetics and other matrices which contains the following reagents for analyzing liquids, undiluted or diluted. This example is carried out in accordance with rows 2 and 3 of TABLE I.

A. A sample of the oil or oil containing extracts is dissolved or mixed in a preparation reagent such as isopropanol, with or without protectants. This sample may be processed through membranes in accordance with rows 2 or 3 of TABLE I.

B. A first dye sensitive to concentration of acid for its spectral properties such as Xylenol Orange soluablized in isopropanol with protectants, as necessary, or in other solvents such as isopropanol/water mixtures, hexane, methanol/isopropanol mixtures.

C A second dye such as Xylenol Orange or non-oxidized hemoglobin combined with certain pro-oxidants (e.g., acidified iron) such that it will react with lipid peroxides. is solubilized in the same solvent system as was used for the and the same solvent system used for the first dye in paragraph B (above) of this example, a second reagent.

D. A control or standard prepared from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

E. The solutions from steps (A and B), (A and C), (D and B) and (D and C) are combined and read spectrally at the peak most sensitive to acidity of the dye, and the results of such readings are compared to results obtained from the standards and the peroxide reaction is read at that peak for the electron recipient at 570 nm.

F. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid (e.g., by a log-logit curve plot). For lipid peroxides the absorption of Xylenol Orange-Fe Complex increases at 570 nm as it receives electrons. This absorption can be read utilizing any spectral device measuring absorption at the particular wavelength G. Sample blanks can be run if necessary for very colored substances as can blanks for standards.

Example 10

Lipid Peroxides and Free Fatty Acids in Oils and Oil Components

A test kit for qualitative or semi-quantitative determination of lipid peroxides and free fatty acids in oils and/or oil components of food, personal care, cosmetics and other matrices which contains the following reagents for analyzing liquids, undiluted or diluted. The test kit contains the reagents and membranes set forth herebelow and in rows 2 or 3 of TABLE I.

A. A sample of the oil or oil containing extracts is dissolved or mixed in a preparation reagent such as isopropanol, with or without protectants. This sample is then processed through membranes in accordance with rows 2 or 3 of TABLE I. Such membrane processing may be performed using a test apparatus of the present invention, as described above.

B. A first dye sensitive to concentration of acid for its spectral properties such as Xylenol Orange soluablized in isopropanol with protectants, as necessary, or in other solvents such as isopropanol/water mixtures, hexane, methanol/isopropanol mixtures.

C A second dye such as Xylenol Orange or non-oxidized hemoglobin combined with certain prooxidants (e.g., acidified iron) such that it will react with lipid peroxides, is solubilized in the same solvent system as was used for the and the same solvent system used for the first dye in paragraph B (above) of this example, a second reagent.

D. A control or standard prepared from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

E. The solutions from steps (A and B), (A and C), (D and B) and (D and C) are combined and read spectrally at the peak most sensitive to acidity of the dye, and the results of such readings are compared to results obtained from the standards and the peroxide reaction is read at that peak for the electron recipient at 570 nm.

F. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid (e.g., by a log-logit curve plot). For lipid peroxides the absorption of Xylenol Orange-Fe Complex increases at 570 nm as it receives electrons. This absorption can be read utilizing any spectral device measuring absorption at the particular wavelength G. Sample blanks can be run if necessary for very colored substances as can blanks for standards.

Example 11

Lipid Peroxides and Free Fatty Acids in Oils and Oil Components

A test kit for utilizing a novel chemical test to qualitatively or quantitatively determine lipid peroxides and free fatty acids in oils or oil components of foods, personal care products, cosmetics and other matrices. The test kit includes the reagents and membranes specified below and in row 3 of TABLE I.

A. A sample of the oil or oil containing extracts is dissolved or mixed in a preparation reagent such as isopropanol, with or without protectants. This sample may or may not be processed through a membrane, in accordance with row 3 of TABLE I. If performed, such membrane processing may be carried out using a test apparatus of the present invention, as described above.

B. A first dye sensitive to concentration of acid for its spectral properties such as Xylenol Orange or Thyrnol blue (or another dye with sensitivity to small pH changes in the pH 6 to pH 8 range) is solubilized in a solvent such as isopropanol, with protectants as necessary.

C. A second dye such as Xylenol Orange or non oxidized hemoglobin in the presence of a prooxidant such as acidified iron, is solubilized in the same solvent system as the first dye of paragraph B of this example. This second dye will react with lipid peroxides or can be altered by lipid peroxides and then interact with XO, Hemoglobin or other sensitive reagents.

D. A control or standard prepared from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

E. Concentration is determined by visual comparison of the color of the samples to standard solutions or a color wheel or chart. For free fatty acids the reagent is initially blue but turns yellow as the acidity increases. For lipid peroxides, the dye is initially yellow but turns blue as lipid peroxide concentration ioncreases—reaching a deep blue at 20 Meq/kg.

G. Sample blanks can be run if necessary for very colored substances as can blanks for standards.

Example 12

Semi-Quantitative Test for Lipid Peroxides and Free Fatty Acids in Oils or Oil Components A test kit for semi-quantitative determination of lipid peroxides and free fatty acids in oils or oil components of a food, personal care product, cosmetic or other matrix, using a color wheel. The test kit includes the reagents and membranes (if necessary) described herebelow and in rows 2 or 3 of TABLE I. This test os particularly useful for analyzing liquids, undiluted or diluted, and may be used to classify samples of olive oil (i.e., extra virgin, virgin, virgin corriente) or to sub-categorize samples of olive oil within a particular class based on expected shelf life.

A. A sample of the oil or oil containing extracts is dissolved or mixed in a preparation reagent such as isopropanol, with or without protectants. This sample may or may not be processed through a membrane, in accordance with row 3 of TABLE I. If performed, such membrane processing may be carried out using a test apparatus of the present invention, as described above.

B. A first dye sensitive to concentration of acid for its spectral properties such as Xylenol Orange or Thyrnol blue (or another dye with sensitivity to small pH changes in the pH 6 to pH 8 range) is solubilized in a solvent such as isopropanol, with protectants as necessary.

C. A second dye such as Xylenol Orange or non oxidized hemoglobin in the presence of a prooxidant such as acidified iron, is solubilized in the same solvent system as the first dye of paragraph B of this example. This second dye will react with lipid peroxides or can be altered by lipid peroxides and then interact with XO, Hemoglobin or other Sensitive reagents.

D. A control or standard prepared may from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

E. The solutions from steps (A and B) and (A and C) are combined and the colors which develop in those admixtures are visually compared to those of a color wheel or color chart. Alternatively, a spectral determination could be used, in which case the solutions from steps (D and B) and (D and C) will also be combined and mixed with the reagents, and the absorption of the sample solutions will be compared to the absorptions of the standard solutions to arrive at determinations of lipid peroxides and free fatty acids in the samples.

F. For Xylenol Orange between 0.001% to 10.0% in isopropanol this peak is between blue and when acidified is yellow.

G. Sample blanks can be run if necessary for very colored substances as can blanks for standards.

Example 13

A Test for Lipid Peroxides and Free Fatty Acids in Olive Oils to Predict Shelf Life and Quality A test kit for qualitative or quantitative determination of lipid peroxides and free fatty acids oils or oil components of a food, personal care product, cosmetic or other matrix, using a spectrophotometer. The test kit includes the reagents and membranes (if necessary) described herebelow and in rows 2 or 3 of TABLE I. This test is particularly useful for analyzing liquids, undiluted or diluted, and may be used to classify samples of olive oil (i.e., extra virgin, virgin, virgin corriente) or to sub-categorize samples of olive oil within a particular class based on expected shelf life.

A. A sample of the oil or oil containing extracts is dissolved or mixed in a preparation reagent such as isopropanol, with or without protectants. This sample may or may not be processed through a membrane, in accordance with row 3 of TABLE I. If performed, such membrane processing may be carried out using a test apparatus of the present invention, as described above.

B. A first dye sensitive to concentration of acid for its spectral properties such as Xylenol Orange or Thyrnol blue (or another dye with sensitivity to small pH changes in the pH 6 to pH 8 range) is solubilized in a solvent such as isopropanol, with protectants as necessary.

C. A second dye such as Xylenol Orange or non oxidized hemoglobin in the presence of a pro-oxidant such as acidified iron, is solubilized in the same solvent system as the first dye of paragraph B of this example. This second dye will react with lipid peroxides or can be altered by lipid peroxides and then interact with XO, Hemoglobin or other sensitive reagents.

D. A control or standard prepared may from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

E. The solutions from steps (A and B) and (A and C) are combined and those admixtures are read spectrophotometrically at 570 nm or at the wavelength for hemoglobin. The absorption of the test samples is compared to the absorption of the standards to determine the concentration of free fatty acids and lipid peroxides.

F. For Xylenol Orange between 0.001% to 10.0% in isopropanol this peak is between 540 and 600 urn with the optimal choice at 570 nm. A decrease in the absorption at this peak increases with acidity on a logarithmic basis and this is used to determine the free fatty acid for the oil (i.e. a log-logit curve plot). This can be done utilizing any spectral device measuring absorption at the particular wavelength G. Sample blanks can be run if necessary for very colored substances as can blanks for standards.

H. The quality and shelf life of each sample is then classified as follows:

| Quality Classification | Shelf Life Prediction |
| --- | --- |
| FFA = 0–1% extra virgin | LPO = 0–6 Meq/Kg 18 months |
| FFA = 1–2% virgin | LPO = 6–12 Meq/Kg 12 months |
| FFA = 2–3% virgin common | LPO = 12–20 Meq/Kg 6 months |
| FFA = >3% not consumable | LPO = >20 Meq/Kg not consumable |

I. It will be appreciated that, as an alternative to spectral determinations, semi-quantitative determinations of FFA and LPO may be made using colored standards, color charts or a color wheel, and the quality classification and shelf life prediction can be arrived at based on a sheme of visual color combinations or shades.

Example 14

A Test for Free Fatty Acids, Lipid Peroxides, and Polyphenols in Oil and Oil Components to Determine if the Oil is Adulterated or Aged A test kit for qualitatively determining the amount of free fatty acids and LPO in oils and oil components in foods, in combination with a polyphenol test which together determines if the olive oil has been adulterated and is aged. This test is performed in accordance with row 30 of TABLE I and the test kit includes the reagents and membranes described below and in row 30 of TABLE I.

A. A sample of the oil or oil containing extracts is dissolved or mixed in a preparation reagent such as isopropanol, with or without protectants, and processed through the membranes shown on row 30 of TABLE I.

B. A first dye sensitive to concentration of acid for its spectral properties, such as Xylenol Orange, solubilized in a solvent such as isopropanol, with protectants as necessary, is provided for determination of free fatty acids.

C. A second dye sensitive to polyphenol, such as folin ciocalteau reagent in water/isopropanol with sodium carbonate, is provided to determine the polyphenol concentration.

D. A third dye or indicator, such as Xylenol Orange combined with acidified iron, which is sensitive to free electron transfer from lipid peroxides is provided to determine lipid peroxides.

E. A control or standard prepared may from free fatty acids or prepared oil and standard compounds in isopropanol at specified concentrations of free fatty acids from 0.00% to 5.00% and controls or standards or controls with lipid peroxides prepared from hydrogen peroxide or cumeneperoxide or other stable or relatively stable peroxides at concentrations of 1 nmol/ml to 1000 nmol/ml.

F. The solutions of (A and B) and (A and C) and (A and D) are combined, and the color of each of the resulting admixtures is determined spectrally, or by visual comparison to known standards, color chart or color wheel.

F. For Xylenol Orange between 0.001% to 10.0% in isopropanol this color is first blue and then at 1.0% free fatty acid yellow so that an olive oil can be immediately labeled as not extra virgin or a cooking oil can be labeled as no longer usable.

G. An adjustment in the Xylenol Orange concentration and a change for blue to yellow can be seen for 1.0 to 3.0 free fatty acid. Polyphenols from 2 to 200 micrograms per gram are determined H. The results of this test allow the oil to be categorized as follows:

| 1. Quality Based on FFA Concentration: | |
|---|---|
| FFA = 0–1% | extra virgin |
| FFA = 1–2% | virgin |
| FFA = 2–3% | virgin common |
| FFA = >3% | not consumable |
| 2. Aging Based on LPO Concentration: | |
| LPO = 0–6 Meq/Kg | Minimal Aging - 18 months left |
| LPO = 6–12 Meq/Kg | Some Aging - 12 months left |
| LPO = 12–20 Meq/Kg | Maximum Acceptable Aging - 6 months left |
| LPO = >20 Meq/Kg | Aged - not consumable |
| 3. Adulteration Based on Polyphenol × FFA: | |
| PP × FFA = 75 | Unadulterated Extra Virgin |
| PP × FFA = 125 | Unadulterated Virgin |
| PP × FFA = 150 | Unadulterated Virgin Common |
| PP × FFA = 37 | 50% adulterated Extra Virgin |
| PP × FFA = 35 | 50% adulterated Virgin |
| PP × FFA = 75 | 50% adulterated Virgin Common |
| PP × FFA = 1.5 | 90% adulterated Extra Virgin |
| PP × FFA = 3.0 | 90% adulterated Virgin |
| PP × FFA = 9.0 | 90% adulterated Virgin Common |

Example 15

Lipid Peroxides and Free Fatty Acids in Oils and Oil Components

A test kit for determining the amount of lipid peroxides and free fatty acids in oils and oil components either qualitatively or quantitatively in food, personal care, cosmetics and other matrices which contains the following reagents for analyzing liquids undiluted or diluted and which allow assignment to categories for olive oil as well as levels within extra virgin which have longer expected shelf life or within virgin or within virgin common using colorwheels A. The oil or oil containing extracts in isopropanol with or without protestants B. A dye sensitive to concentration of acid for its spectral properties such as Xylenol Orange is soubilized in isopropanol, with protectants as necessary. A second indicator reagent, such as Xylenol Orange or non oxidized hemoglobin in the presence of a pro-oxidant, is provided to determine lipid peroxides. This lipid peroxide reagent typically requires a pro-oxidant such as acidified iron or iron complex to initiate the transfer of electrons from the lipid peroxides to the final substrate.

C. A control or standard prepared may from free fatty acids or prepared oil and standard compounds in isopropanol at specified concentrations of free fatty acids from 0.00% to 5.00%. Controls or standards for lipid peroxides are prepared from hydrogen peroxide or cumeneperoxide or other stable or relatively stable peroxides at concentrations of 1 nmol/ml to 1000 nmol/ml.

D. The solutions from steps (A and B) and (C and B) are combined and the color developed in those solutions are compared to the standards or to a color wheel to determine free fatty acids and lipid peroxides.

E. For Xylenol Orange at concentrations between 0.001% to 10.0% in isopropanol, the indicator solution is initially blue and changes to yellow in the presence of a predetermined concentration of free fatty acids. When Xylenol Orange is also used (w/acidified iron) to indicate polyphenols, the solution is initially yellow but changes to deep blue in the presence of polyphenols at 20 Meq/Kg or more.

G. Sample blanks can be run if necessary for very colored substances as can blanks for standards Example 16

Lipid Peroxides and Free Fatty Acids in Oils and Oil Components

A test kit for determining the amount of lipid peroxides and free fatty acids in oils and oil components either qualitatively or quantitatively in food, personal care, cosmetics and other matrices which contains the following reagents for analyzing liquids undiluted or diluted and which allow assignment to categories for olive oil as well as levels within extra virgin which have longer expected shelf life or within virgin or within virgin common based on LPO and FFA.

A. The oil or oil containing extracts in isopropanol with or without Protectants.

B. A dye sensitive to concentration of acid for its spectral properties such as Xylenol Orange solubilized in isopropanol with protectants as necessary and a second reagent such as Xylenol Orange or non-oxidized hemoglobin which in the presence of certain prooxidants can react with lipid peroxides. The lipid peroxide reagent requiring acidified iron or iron complex to initiate the transfer of electrons from the lipid peroxides to the final substrate.

C. Controls or standards may be prepared for from free fatty acids or prepared oil and standard compounds, in isopropanol at specified concentrations of free fatty acids from 0.00% to 5.00%. Controls or standards for lipid peroxides are prepared from hydrogen peroxide or cumeneperoxide or other stable or relatively stable peroxides at concentrations of 1 nmol/ml to 1000 nmol/ml.

D. The solutions from steps (A and B) and (C and B) are combined and the color developed in those solutions and in the standards are read at that peak for the electron recipient either 570 nm or the wavelength for hemoglobin.

E. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid for the oil (i.e. a log-logit curve plot). This can be done utilizing any spectral device measuring absorption at the particular wavelength F. Sample blanks can be run if necessary for very colored substances as can blanks for standards.

H. Based on the results obtained, the oil samples may be classified as follows:

| Free Fatty Acid | Lipid Peroxide |
|---|---|
| 0 to 1% = extra virgin | 0 to 6 Meq/Kg = long shelf life |
| 1 to 2% = virgin | 6 to 12 Meq/Kg med = shelf life |
| 2 to 3% = virgin common | 12 to 20 Meg/Kg = short shelf life |
| >3% = not consumable | >20 Meq/Kg = not consumable |

Example 17

Free Fatty Acids in Oils and Oil Components

A test kit for determining the amount of free fatty acids in oils and oil components in food, personal care, cosmetics and other matrices which contains the following reagents for analyzing liquids undiluted or diluted. Utilizing a single or stacked membrane preparation of the matrix to remove particulates, protein, or other interferents.

A. The oil or oil containing extracts are solubilized in isopropanol, with or without protectants, and passed through a first membrane (e.g., MCE 0.45 micron or Durapore 0.45 micron) with or without a second membrane. The test apparatus of the present invention may be used for this membrane processing.

B. A second membrane being used if necessary to remove additional compounds which would bind with the substrate sensitive to acidity or to bind in organic acids which could contribute background acidity levels.

C. A dye sensitive to concentration of and for its spectral properties such as Xylenol Orange solubilized in isopropanol with protectants as necessary.

D. A control or standard prepared from free fatty adds or prepared oil and standard compounds in isopropanol at specified level of free fatty acids of 0.00% to 5.00% free fatty adds.

E. Where A and B or C and B are combined and read at the peak most sensitive to acidity of the dye and results of samples are compared to results obtained from the standards.

F. For Xylenol Orange between 0.001% to 10.0% in isopropanol, this peak is between 540 and 600 nm with the optimal choice at 57 nm. A decrease in the absorption at this peak increases with acidity on a logarithmic basis, and this is used to determine the free fatty acid for the oil (i.e. a log-logit curve plot.) This can be done utilizing any spectral device measuring absorption at the particular wavelength.

G. Sample blanks can be run if necessary for very colored substances as can blanks for standards.

Example 18

Free Fatty Acids in Oils and Oil Components

A test kit for determining the amount of free fatty acids in oils and oil components in food, personal care, cosmetics and other matrices which contains the following reagents for analyzing liquids undiluted or diluted.

A. The oil or oil containing extracts are soluabilized in isopropanol, with or without proteceants.

B. A dye sensitive to concentration of acid for it's spectral properties, such as Xylenol Orange or Thymol Blue (or other dyes which undergo color changes in the pH 6 to 8 range) is solubilized in isopropanol, with protestants as necessary, and with buffering to increase sensitivity.

C. A control or standard prepared from free fatty acids or prepared oil and standard compounds in isopropanol at specified level of free fatty acids of 0.00% to 5.00% free fatty ends.

D. Where A and B or C and B are combined and read at the peak most sensitive to acidity of the dye and results of samples are compared to results obtained from the standards.

E. For Xylenol Orange between 0.001% to 10.0% in isopropanol this peak is between 540 and 600 nm with the optimal choice at 570 nm. A decrease in the absorption at this peak increases with acidity on a logarithmic basis and this is used to determine the free fatty acid for the oh (i.e. a log-logit curve plot.) This can be done utilizing a spectral device measuring absorption at the particular wavelength.

F. Sample blanks can be non if necessary for very colored substances as can blanks for standards.

Example 19

Qualitative Determination of Free Fatty Acids in Oils and Oil Components

A test kit for qualitatively determining the amount of free fatty acids in oils and oil components in food, personal care, cosmetics and other matrices which contains the following reagents for analyzing liquids undiluted or diluted.

A. The oil or oil containing extracts is solubilized in isopropanol, with or without protestants. The oil sample may be obtained from a bottle of oil at restaurant, at home, during preparation etc.

B. A dye sensitive to concentration of acid for its spectral properties such as Xylenol Orange is solubilized In isopropanol, with protectants as necessary.

C. A control or standard, if necessary, is prepared from free fatty acids or prepared oil and standard compounds in isopropanol, at specified free fatty acid concentrations (e.g., 0.00% to 5.00%).

D. The solutions obtained in steps (A and B) and (C and B) are combined and the color shift in each such solution is read visually. The results of samples are compared to results obtained from the standards, if necessary, or to a visual chart or color wheel.

E. For Xylenol Orange between 0.001% to 10.0% in isopropanol this color is first blue and then at 1.0% free fatty acid yellow so that an olive oil can be immediately labeled as not extra virgin or a cooking oil can be labeled as no longer usable F. An adjustment in the Xylenol Orange concentration and a change for blue to yellow can be seen for 1.0 to 3.0 free fatty acid.

It will be appreciated that the invention has been described hereabove with reference to certain preferred embodiments and examples. It is to be appreciated however, that these preferred embodiments and examples are not exhaustive, and no effort has been made to specifically describe each and every embodiment or example of the invention. It is, however, intended that all embodiments and examples which are within the spirit and scope of the invention, be included within the scope of the following claims.

What is claimed is:

1. An apparatus for non-electrophoretic determination of the presence of at least one analyte in at least one flowable sample, said apparatus comprising:

a housing having a cavity formed therein;

at least one filtrate-receiving vessel positioned within the cavity of the housing, the filtrate-receiving vessel having an open end;

at least one membrane module positioned over the open end of the at least one filtrate-receiving vessel, the at least one membrane module having portions formed of a first hard material and portions formed of a second elastomeric material;

at least one sample-receiving well, each sample-receiving well being positioned in association with one of said membrane components such that sample place within a particular sample receiving well is filtered through the associated membrane module, and a filtrate which emerges from that membrane module will be received within the associated filtrate-receiving vessel;

a cover for sealing said cavity of said housing, the cover having at least one sample port bounded by a rim extending from the surface of the lid away from the cavity, wherein the rim is structured to retain the at least one membrane module such that the portions of the at least one membrane module that are formed of elastomeric material interact with the rim to provide substantially air tight sealing between the membrane module and the rim; and a differential pressure source to cause a pressure differential between each of said sample-receiving wells and each of said filtrate-receiving vessels, said pressure differential being operative to drive each sample through the associated membrane module and the resultant filtrate into the associated filtrate-receiving vessel.

2. The apparatus of claim 1 wherein said pressure source provides negative pressure within the cavity of said, housing so as to pull the filtrate through each membrane component.

3. The apparatus of claim 1 wherein said pressure source provides positive pressure within the samples wells so as to push the filtrate through each membrane component.

4. The apparatus of claim 2 further comprising:

at least one air-inlet opening formed in said apparatus, the air inlet openings being associated with each one of said sample-receiving wells, such that when a particular sample-receiving well becomes empty air will be drawn through the associated air inlet opening.

5. The apparatus of claim 1 wherein the differential pressure source comprises a pump which is integral of the apparatus.

6. The apparatus of claim 5 wherein said pump integral of the apparatus is a vacuum pump which is incorporated within said housing.

7. The apparatus according to claim 1 wherein the at least one membrane module comprises a plurality of membrane modules, and at least two of the membrane modules are configured so as to nest within one another when stacked, thereby ensuring proper alignment of the membrane to allow sample to flow through each sample flow channel.

* * * * *